(12) United States Patent
Morimoto et al.

(10) Patent No.: US 11,246,195 B2
(45) Date of Patent: Feb. 8, 2022

(54) LIGHT SOURCE APPARATUS AND ENDOSCOPE SYSTEM

(71) Applicant: FUJIFILM Corporation, Tokyo (JP)

(72) Inventors: Yoshinori Morimoto, Ashigarakami-gun (JP); Satoshi Ozawa, Ashigarakami-gun (JP); Eiji Ohashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 631 days.

(21) Appl. No.: 16/105,248

(22) Filed: Aug. 20, 2018

(65) Prior Publication Data

US 2019/0013444 A1    Jan. 10, 2019

Related U.S. Application Data

(62) Division of application No. 14/505,293, filed on Oct. 2, 2014, now abandoned.

(30) Foreign Application Priority Data

Oct. 3, 2013  (JP) ................................. 2013-208215

(51) Int. Cl.
*H01L 33/50*  (2010.01)
*H01L 33/58*  (2010.01)
(Continued)

(52) U.S. Cl.
CPC ......... *H05B 45/12* (2020.01); *A61B 1/00057* (2013.01); *A61B 1/0638* (2013.01);
(Continued)

(58) Field of Classification Search
CPC ..... H01L 33/50; H01L 33/58; H01L 33/0854; H01L 27/15; H01L 2224/49107;
(Continued)

(56) References Cited

U.S. PATENT DOCUMENTS 8,337,400 B2   12/2012   Mizuyoshi
8,506,478 B2   8/2013    Mizuyoshi
(Continued)

FOREIGN PATENT DOCUMENTS

GB   2493994 A      2/2013
JP   2006-26135 A   2/2006
(Continued)

OTHER PUBLICATIONS

Extended European Search Report, dated Feb. 20, 2015, for European Application No. 14186397.7.
(Continued)

*Primary Examiner* — Timothy J Neal
*Assistant Examiner* — Genja M Frankert
(74) *Attorney, Agent, or Firm* — Birch, Stewart, Kolasch & Birch, LLP

(57) ABSTRACT

A fluorescent type of green light source of a semiconductor in a light source apparatus for an endoscope includes a blue excitation light source device and green emitting phosphor. The blue excitation light source device emits blue excitation light. The green emitting phosphor is excited by the blue excitation light, and emits green fluorescence. A dichroic filter in a dichroic mirror cuts off the blue excitation light from an emission spectrum of mixed light of the blue excitation light and green fluorescence from the fluorescent type of green light source. Thus, illumination light with the emission spectrum of a target can be stably supplied without influence of the blue excitation light to a light amount of blue light from a blue light source of a semiconductor.

18 Claims, 28 Drawing Sheets

(51) Int. Cl.
  *H01L 27/15* (2006.01)
  *F21V 8/00* (2006.01)
  *A61B 1/06* (2006.01)
  *G02B 23/24* (2006.01)
  *A61B 1/07* (2006.01)
  *H05B 45/12* (2020.01)
  *A61B 1/00* (2006.01)
  *A61B 1/04* (2006.01)

(52) U.S. Cl.
  CPC .......... *A61B 1/0646* (2013.01); *A61B 1/0653* (2013.01); *A61B 1/0661* (2013.01); *A61B 1/0684* (2013.01); *A61B 1/07* (2013.01); *G02B 6/0005* (2013.01); *G02B 23/2469* (2013.01); *H01L 27/15* (2013.01); *H01L 33/50* (2013.01); *H01L 33/58* (2013.01); *A61B 1/043* (2013.01); *G03B 2215/0567* (2013.01); *H01L 2224/48091* (2013.01); *H01L 2224/49107* (2013.01); *H01L 2924/00012* (2013.01); *H01L 2924/00014* (2013.01); *H01L 2924/181* (2013.01)

(58) Field of Classification Search
  CPC ..... H01L 2924/181; H01L 2224/48091; A61B 1/0661; A61B 1/0646; A61B 1/00057; A61B 1/0684; A61B 1/07; A61B 1/0653; A61B 1/0638; A61B 1/043; G02B 6/0005; G02B 2215/0567; G02B 23/2469
  See application file for complete search history.

(56) References Cited

U.S. PATENT DOCUMENTS

| | | | |
|---|---|---|---|
| 2002/0035330 A1 | 3/2002 | Cline et al. | |
| 2005/0234526 A1* | 10/2005 | Gilhuly | A61B 5/444 607/86 |
| 2008/0283770 A1* | 11/2008 | Takahashi | G02B 23/2461 250/458.1 |
| 2009/0306478 A1* | 12/2009 | Mizuyoshi | H01S 5/0087 600/178 |
| 2010/0280322 A1 | 11/2010 | Mizuyoshi | |
| 2011/0116253 A1* | 5/2011 | Sugiyama | G03B 33/08 362/84 |
| 2011/0116520 A1 | 5/2011 | Krijn et al. | |
| 2011/0237894 A1* | 9/2011 | Ozawa | A61B 1/043 600/168 |
| 2013/0088850 A1 | 4/2013 | Kroell | |
| 2014/0092581 A1 | 4/2014 | Berben | |
| 2015/0003059 A1 | 1/2015 | Haitz et al. | |

FOREIGN PATENT DOCUMENTS

| | | |
|---|---|---|
| JP | 2007-68699 A | 3/2007 |
| JP | 2009-297290 A | 12/2009 |
| JP | 2011-41758 A | 3/2011 |
| JP | 2013-111177 A | 6/2013 |
| WO | WO 2012/167831 A1 | 12/2012 |
| WO | WO 2013/050733 A1 | 4/2013 |
| WO | WO 2013/078463 A1 | 5/2013 |

OTHER PUBLICATIONS

Chinese Office Action and English translation thereof, dated Mar. 1, 2017, for Chinese Application No. 201410524810.7.
Chinese Office Action issued in Chinese Application No. 201410524810.7 dated Aug. 28, 2017, together with an English translation.
Japanese Office Action, dated Dec. 9, 2015, for Japanese Application No. 2013-208215, with English translation.

* cited by examiner

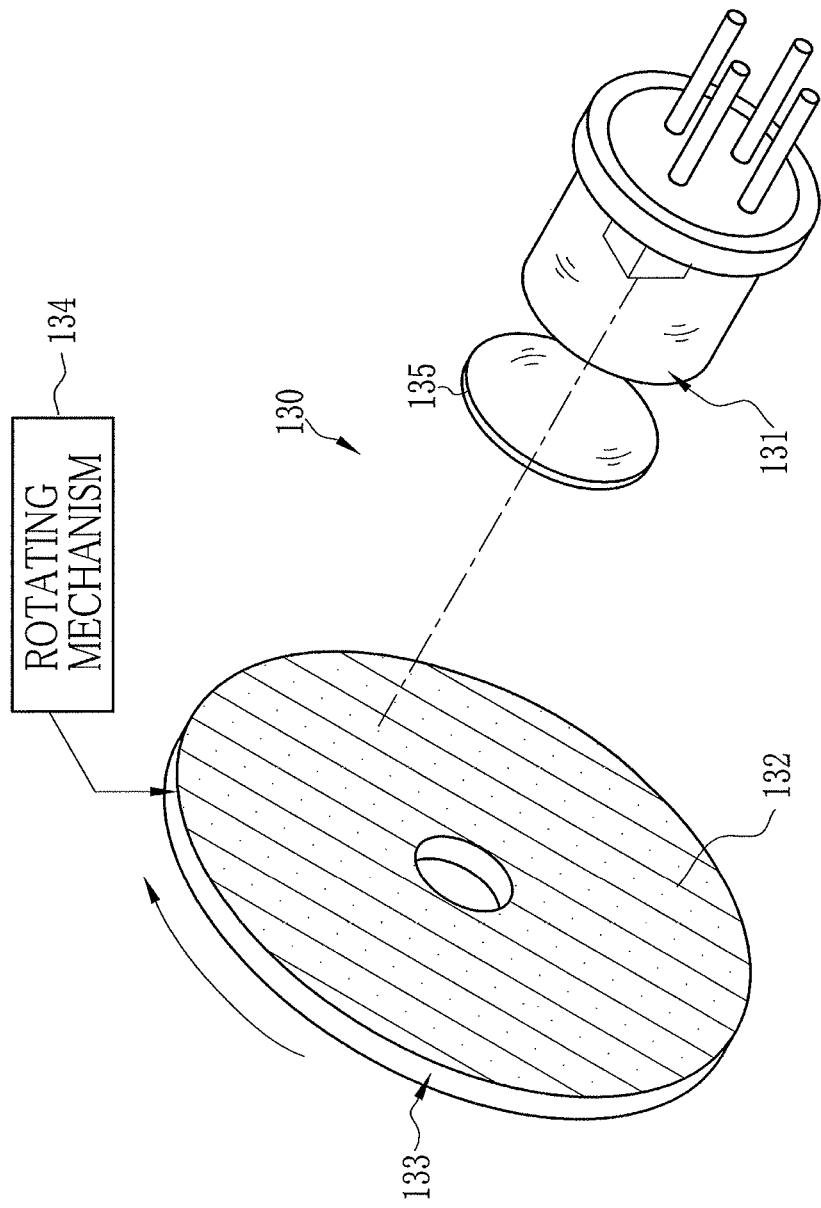

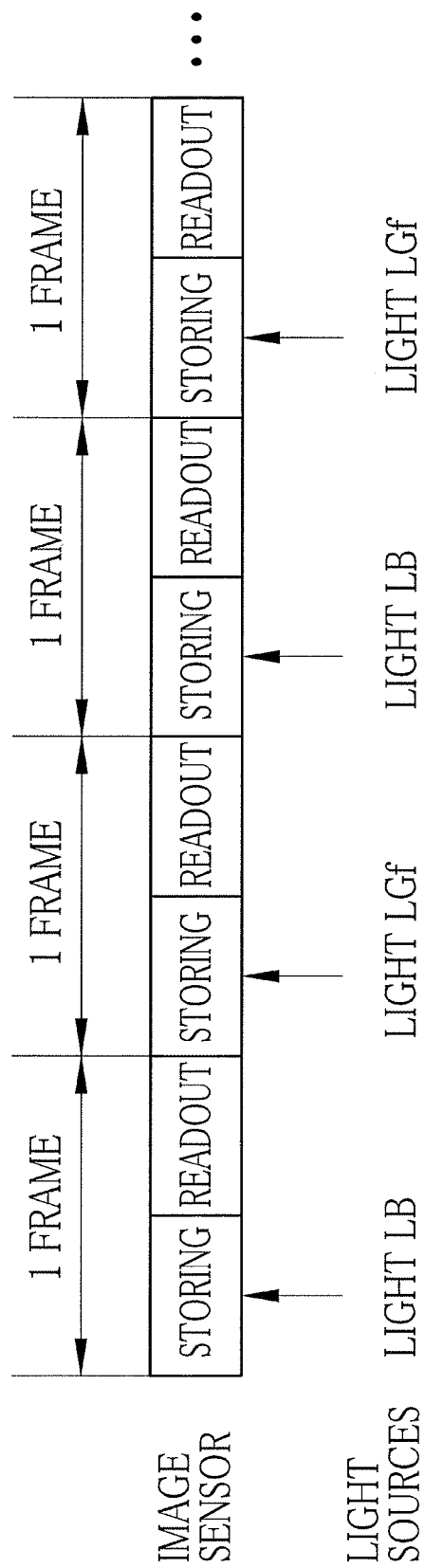

LIGHT SOURCE APPARATUS AND ENDOSCOPE SYSTEM

CROSS-REFERENCE TO RELATED APPLICATION

This application is a Divisional of copending application Ser. No. 14/505,293 filed on Oct. 2, 2014, which claims priority under 35 USC § 119 to Japanese Patent Application No. 2013-208215, filed 3 Oct. 2013, the entire contents of both of which are incorporated by reference herein.

BACKGROUND OF THE INVENTION

1. Field of the Invention

The present invention relates to alight source apparatus and endoscope system in which a fluorescent type of green semiconductor light source is used, and illumination light of an emission spectrum of a target for use in endoscopic imaging can be stably obtained.

2. Description Related to the Prior Art

Endoscopic imaging with an endoscope system is widely known in the field of medical diagnosis. The endoscope system includes an endoscope, a light source apparatus and a processing apparatus. The light source apparatus supplies light to the endoscope. The processing apparatus processes an image signal output by the endoscope. The endoscope includes an elongated tube for entry in a body cavity. A tip of the elongated tube has lighting windows and a viewing window. The lighting windows apply the light to an object of interest in the body cavity. The viewing window receives object light from the object of interest for imaging. Alight guide device is incorporated in the endoscope, and includes a fiber bundle of a plurality of optical fibers. The light guide device guides light from the light source apparatus to the lighting windows. An image sensor is disposed behind the viewing window, for example, CCD image sensor. The object of interest illuminated with the light is imaged by the image sensor, which outputs an image signal. The processing apparatus generates a display image of the image signal. A monitor display panel is driven to display the image, to observe the object of interest in the body cavity.

Widely used examples of light sources in the light source apparatus are a xenon lamp and halogen lamp for emitting normal white light. JP-A 2007-068699 and U.S. Pat. Nos. 8,337,400 and 8,506,478 (corresponding to JP-A 2009-297290) disclose use of semiconductor light sources such as laser diodes (LDs), light emitting diodes (LEDs) and the like for the purpose of the endoscopic imaging.

JP-A 2007-068699 discloses the light source apparatus, in which the semiconductor light sources have three LEDs to emit light of blue, green and red. Components of the light of blue, green and red are combined to produce the white light.

In the xenon lamp and halogen lamp, a ratio between light components of blue, green and red in the white light is constant and cannot be adjusted. However, the semiconductor light sources of blue, green and red are controllable for discretely adjusting light amounts of the colors. Illumination light of plural types can be produced easily with various spectra of emission.

Examples of the semiconductor light sources of green include a green semiconductor light source having an element for emitting green light itself, and a fluorescent type of a semiconductor light source. The fluorescent type includes an excitation light source device for emitting excitation light, and green emitting phosphor excited by the excitation light for emitting green fluorescence. For example, U.S. Pat. Nos. 8,337,400 and 8,506,478 disclose a fluorescent type of green semiconductor light source having a blue excitation light source device (blue LED) and green emitting phosphor. The blue excitation light source device emits blue excitation light in a violet to blue wavelength range. The green emitting phosphor is excited by the blue excitation light for emitting green fluorescence of a green wavelength range.

Among various products of LEDs available commercially, a blue-violet LED for lighting in a violet to blue wavelength range is usable more widely than a green LED for lighting in a green wavelength range, because of such advantage that efficiency in the light emission of the blue-violet LED is higher than the green LED, and that its cost is lower. It is conceivable to use the fluorescent type of green semiconductor light source disclosed in U.S. Pat. Nos. 8,337,400 and 8,506,478 with a recently higher concern than the semiconductor light sources or green LED for emitting green light.

Furthermore, narrow band imaging with narrow band light (special light) has been known recently in the field of the endoscopic imaging. The narrow band light is light of a limited wavelength range in contrast with the white light for imaging with the entirety of a surface of body tissue or the object of interest. In the narrow band imaging, depth of penetration of light into the body tissue is characteristically different between plural wavelengths. According to utilization of this characteristic, vessel enhancement imaging is performed to enhance part of blood vessels present in mucosa of the body tissue, as described in JP-A 2011-041758. A state of the blood vessels in abnormal tissue such as a cancer is different from the normal tissue, so that the vessel enhancement imaging is useful for discovering an early state of a cancer in the diagnosis of cancer screening.

Examples of the semiconductor light sources disclosed in JP-A 2011-041758 are a fluorescent type of white semiconductor light source and a green semiconductor light source. The fluorescent type of white semiconductor light source (white LED) emits the white light with a continuous spectrum extending fully in a visible light wavelength range. The green semiconductor light source (green LED) emits light of a green wavelength range of 530-550 nm. A band pass filter is disposed downstream of the fluorescent type of white semiconductor light source, and derives light of a blue wavelength range of 390-445 nm from the white light. In the vessel enhancement imaging, the semiconductor light sources are turned on, so as to apply mixed light of the green light and blue light, the green light being emitted by the green semiconductor light source in the wavelength range of 530-550 nm, the blue light being passed through the band pass filter in the wavelength range of 390-445 nm upon emission of the white light from the fluorescent type of white semiconductor light source. The blue light of this wavelength range is highly absorbed by surface blood vessels present on the epithelium (mucosa surface). The green light of this wavelength range is highly absorbed by subsurface or deep blood vessels disposed deeper than the surface blood vessels. A display image with a high contrast between the blood vessels and other tissue can be obtained.

It is conceivable to combine the structures of in JP-A 2007-068699 and U.S. Pat. Nos. 8,337,400 and 8,506,478 on the basis of the light source apparatus of JP-A 2011-041758 for the purpose of increasing the degree of freedom in the spectrum of the light. According to JP-A 2007-068699, the semiconductor light sources of blue, green and red are used for performing the vessel enhancement imaging with blue light from the blue semiconductor light source and green light from the green semiconductor light source. According to U.S. Pat. Nos. 8,337,400 and 8,506,478, the fluorescent type of green semiconductor light source is used for the green light source. However, the combined construction of the light source apparatus has a drawback in that illumination light of an emission spectrum cannot be stably obtained as a target of the vessel enhancement imaging. In relation to the fluorescent type of green semiconductor light source, the blue excitation light is largely absorbed by the green emitting phosphor. However, part of the blue excitation light is not absorbed by the green emitting phosphor, but passes the green emitting phosphor and becomes emitted to the object of interest together with the green fluorescence. Changing the light amount of the green light may change a light amount of the blue excitation light. As a wavelength range of the blue excitation light is overlapped on a wavelength range of blue light emitted by the blue semiconductor light source, the light amount of the blue light is influenced by the change in the light amount of the green light.

In the endoscopic imaging, light amounts of light of blue, green and red are controlled at a desired ratio in compliance with the purpose of the imaging, to output illumination light of a target spectrum. Assuming that color balance of a display image is changed typically in the vessel enhancement imaging by a change in the emission spectrum of the illumination light, a serious problem arises in incorrectness in the endoscopic imaging. It is highly important to stabilize the output of the illumination light of the target spectrum. Also, exposure control in the imaging is performed. In case the exposure amount of the entirety of the image is too low (underexposure), the light amount of the illumination light is raised. In case the exposure amount of the entirety of the image is too high (overexposure), the light amount of the illumination light is lowered.

In the exposure control for generating light of a spectrum as a target for a predetermined ratio between light amounts of the colors, it is necessary to increase or decrease the total of the light amounts without changing the spectrum of the light. However, in the use of the fluorescent type of green semiconductor light source, changing the light amount of the green fluorescence by increasing the output of the fluorescent type of green semiconductor light source may influence to the light amount of the blue light with the overlap of the wavelength range on that of the blue excitation light. Thus, the spectrum will be changed in an unwanted manner. For those reasons, it is impossible stably to produce illumination light of the spectrum of the target in the use of the fluorescent type of green semiconductor light source. There is no known solution of this problem. It is conceivable to consider an amount of the change in the blue excitation light according to the change in the light amount of the green fluorescence, and to adjust the light amount of the blue light with the overlap of the wavelength range with the blue excitation light by use of the amount of the change. However, control of lighting for this conception will be very complicated and cannot be utilized practically.

In the patent documents indicated above, there is no description on the problem of difficulty in stably obtaining illumination light with a spectrum of a target in use of the fluorescent type of green semiconductor light source of the vessel enhancement imaging. No solution of this problem is known in the field of the endoscopic imaging.

SUMMARY OF THE INVENTION

In view of the foregoing problems, an object of the present invention is to provide a light source apparatus and endoscope system in which a fluorescent type of green semiconductor light source is used, and illumination light of an emission spectrum of a target for use in endoscopic imaging can be stably obtained.

In order to achieve the above and other objects and advantages of this invention, a light source apparatus for supplying a light guide device of an endoscope with light includes a blue semiconductor light source for emitting blue light of a blue wavelength range. A fluorescent type of a green semiconductor light source has a blue excitation light source device and green emitting phosphor, the blue excitation light source device emitting blue excitation light of a violet to blue wavelength range overlapping on the blue wavelength range of the blue light, the green emitting phosphor being excited by the blue excitation light for emitting green fluorescence of a green wavelength range. A wavelength cut-off filter component is disposed between the blue excitation light source device and the light guide device, for cutting off the blue excitation light.

Preferably, furthermore, a path coupler couples two light paths from the blue and green semiconductor light sources together.

Preferably, the wavelength cut-off filter component is disposed on the path coupler, or disposed between the path coupler and the green semiconductor light source.

Preferably, the path coupler includes optics disposed at an intersection point between the two light paths. The wavelength cut-off filter component is a dichroic filter formed on the optics.

Preferably, furthermore, a driver simultaneously drives the blue and green semiconductor light sources for vessel enhancement imaging, to output mixed light of the blue light and the green fluorescence.

Preferably, furthermore, a driver alternately drives the blue and green semiconductor light sources for vessel enhancement imaging, sequentially to output the blue light and the green fluorescence.

Preferably, furthermore, a driver is connected to the blue and green semiconductor light sources, and changeable between simultaneous lighting and field sequential lighting. In the simultaneous lighting, the driver simultaneously drives the blue and green semiconductor light sources for vessel enhancement imaging, to output mixed light of the blue light and the green fluorescence. In the field sequential lighting, the driver alternately drives the blue and green semiconductor light sources for vessel enhancement imaging, sequentially to output the blue light and the green fluorescence.

Preferably, the blue semiconductor light source emits the blue light with a peak wavelength of at least one of 405, 415, 430 and 460 nm.

Preferably, furthermore, a measurement sensor measures a light amount of the blue light or the green fluorescence emitted by at least one of the blue and green semiconductor light sources. An optical path device guides part of the blue light or the green fluorescence to the measurement sensor. A light source controller controls power supplied to the blue or green semiconductor light source according to a measurement result of the measurement sensor.

Preferably, the measurement sensor and the optical path device are associated with the green semiconductor light source, and the light source controller adjusts the power supplied to the blue excitation light source device according to the measurement result.

Preferably, furthermore, a band pass filter is disposed upstream of the measurement sensor, for receiving light emitted by the green semiconductor light source and reflected by the optical path device, and cutting off light with a wavelength different from the green wavelength range of the green fluorescence.

In another preferred embodiment, the wavelength cut-off filter component is a wavelength cut-off filter of a plate shape disposed between the green semiconductor light source and the optical path device.

Preferably, the optical path device includes a transparent glass plate, disposed downstream of the blue or green semiconductor light source, for reflecting the part of the blue light or the green fluorescence by Fresnel reflection, to guide the part to the sensor.

Preferably, furthermore, a rotatable disk has the green emitting phosphor formed on a surface thereof. The blue excitation light source device emits the blue excitation light toward the rotatable disk being rotated at an eccentric point thereof.

Also, an endoscope system is provided, including an endoscope having a light guide device for guiding light, and a light source apparatus for supplying the light guide device with the light. The light source apparatus includes a blue semiconductor light source for emitting blue light of a blue wavelength range. A fluorescent type of a green semiconductor light source has a blue excitation light source device and green emitting phosphor, the blue excitation light source device emitting blue excitation light of a violet to blue wavelength range overlapping on the blue wavelength range of the blue light, the green emitting phosphor being excited by the blue excitation light for emitting green fluorescence of a green wavelength range. A wavelength cut-off filter component is disposed between the blue excitation light source device and the light guide device, for cutting off the blue excitation light.

Consequently, illumination light of an emission spectrum of a target for use in endoscopic imaging can be stably obtained, because the wavelength cut-off filter component cuts off a part of the blue excitation light traveling in an unwanted manner.

BRIEF DESCRIPTION OF THE DRAWINGS

The above objects and advantages of the present invention will become more apparent from the following detailed description when read in connection with the accompanying drawings, in which:

FIG. 41 is a perspective view illustrating a sixth preferred embodiment with a green semiconductor light source;

FIG. 42 is a timing chart illustrating lighting and imaging according to the vessel enhancement imaging and field sequential lighting.

DETAILED DESCRIPTION OF THE PREFERRED EMBODIMENT(S) OF THE PRESENT INVENTION

Figure 1:
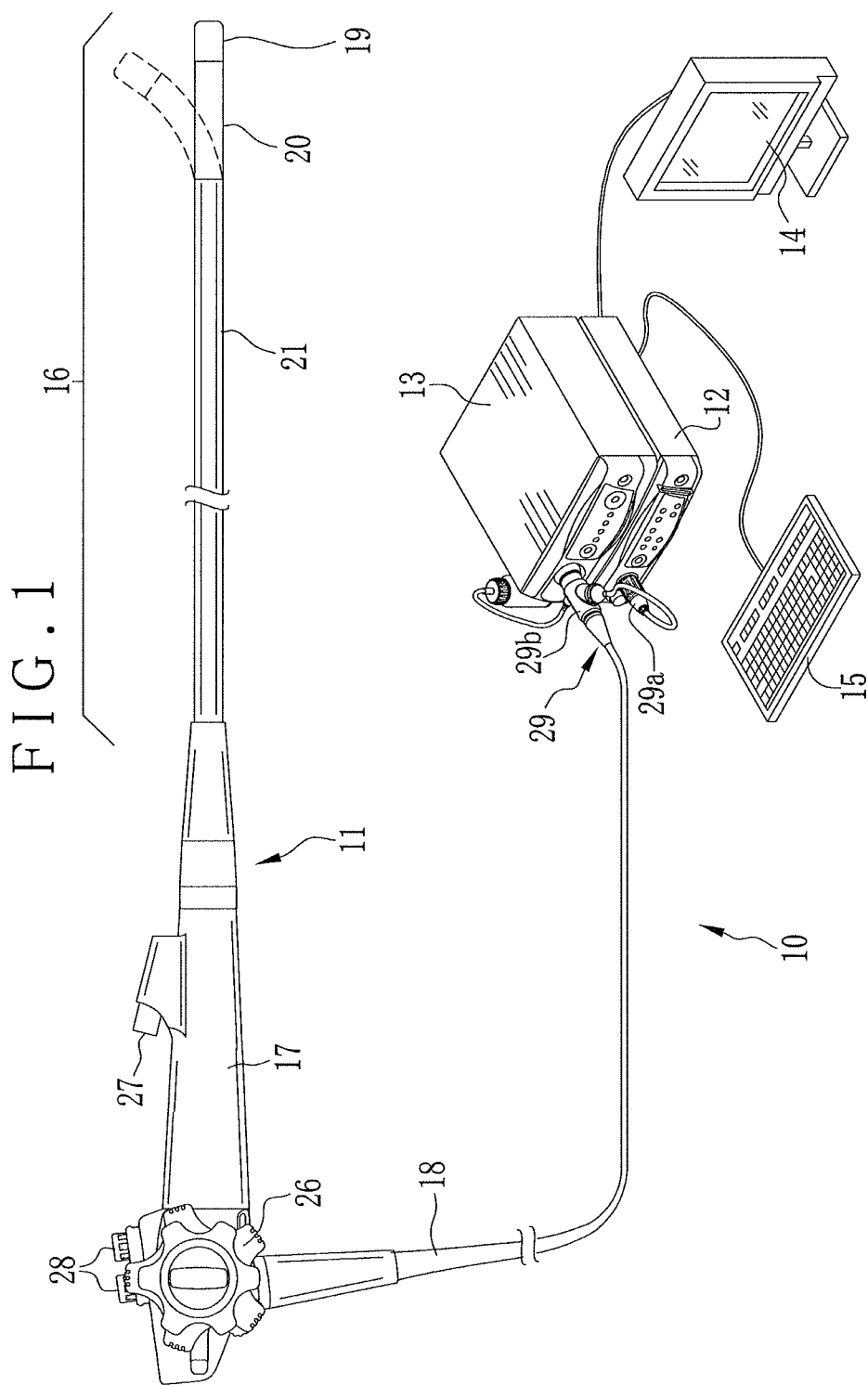
FIG. 1 is an explanatory view in a perspective illustrating an endoscope system.

In FIG. 1, an endoscope system 10 includes an endoscope 11, a processing apparatus 12, a light source apparatus 13 and a monitor display panel 14. The endoscope 11 images an object of interest or body tissue. The processing apparatus 12 receives an image signal from the endoscope 11 and produces an image of the object of interest. The light source apparatus 13 supplies light of illumination to the endoscope 11. The display panel 14 displays the image from the processing apparatus 12. A user input interface 15 is connected to the processing apparatus 12, inclusive of a keyboard, mouse and other input devices.

The endoscope system 10 is changeable between a normal imaging mode for imaging an object of interest, and a vessel enhancement imaging mode for enhancing and imaging blood vessels present in mucosa as object of interest. In the vessel enhancement imaging mode, a pattern of blood vessels is recorded as blood vessel information, for use in diagnosis of a benign or malignant tumor. In the vessel enhancement imaging mode, the object of interest is illuminated with light containing components of a particular wavelength range having a high absorption coefficient in relation to hemoglobin in blood. In the normal imaging mode, a normal multi-color image is produced with suitability for general diagnosis of the object of interest. In the vessel enhancement imaging mode, a vessel enhancement image is produced with suitability for diagnosing the pattern of blood vessels.

The endoscope 11 includes an elongated tube 16, a grip handle 17 and a universal cable 18. The elongated tube 16 is entered in a body cavity of a patient, for example, gastrointestinal tract. The grip handle 17 is disposed at a proximal end of the elongated tube 16. The universal cable 18 connects the endoscope 11 to the processing apparatus 12 and the light source apparatus 13.

Figure 2:
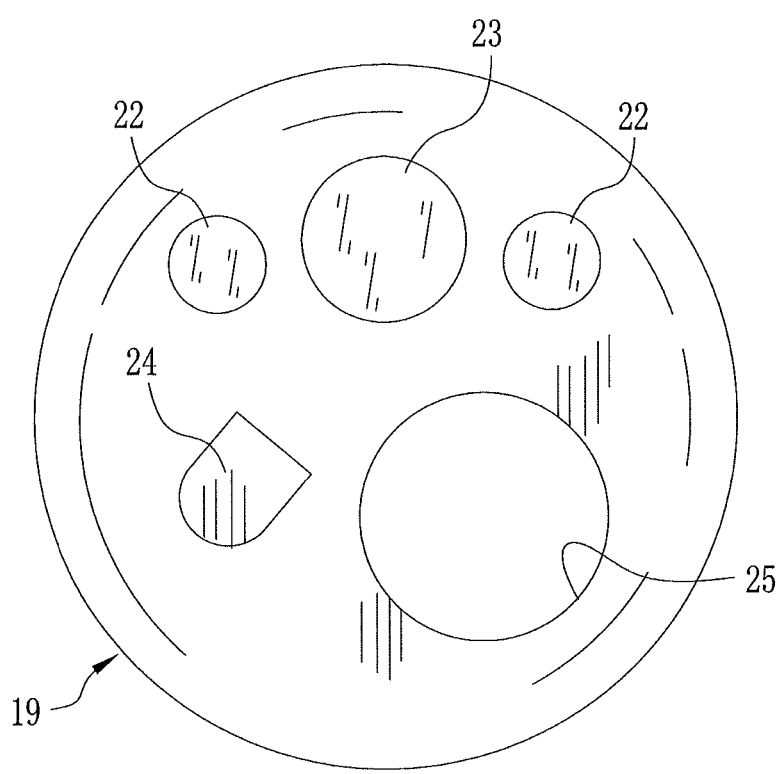
FIG. 2 is a front elevation illustrating a tip of an endoscope.

The elongated tube 16 includes a tip device 19, a steering device 20 and a flexible device 21 arranged in a proximal direction. In FIG. 2, various elements are disposed on an end surface of the tip device 19, including lighting windows 22, a viewing window 23, a nozzle spout 24 for washing fluid, and a distal instrument opening 25. The lighting windows 22 apply illumination light to an object of interest. The viewing window 23 receives image light from the object of interest. The nozzle spout 24 supplies air or water to clean up the viewing window 23. The distal instrument opening 25 is used to protrude a medical instrument such as a forceps, electrocautery device and the like for treatment of various types. An image sensor 56 and an objective lens 60 are disposed behind the viewing window 23. See FIG. 3.

Figure 3:
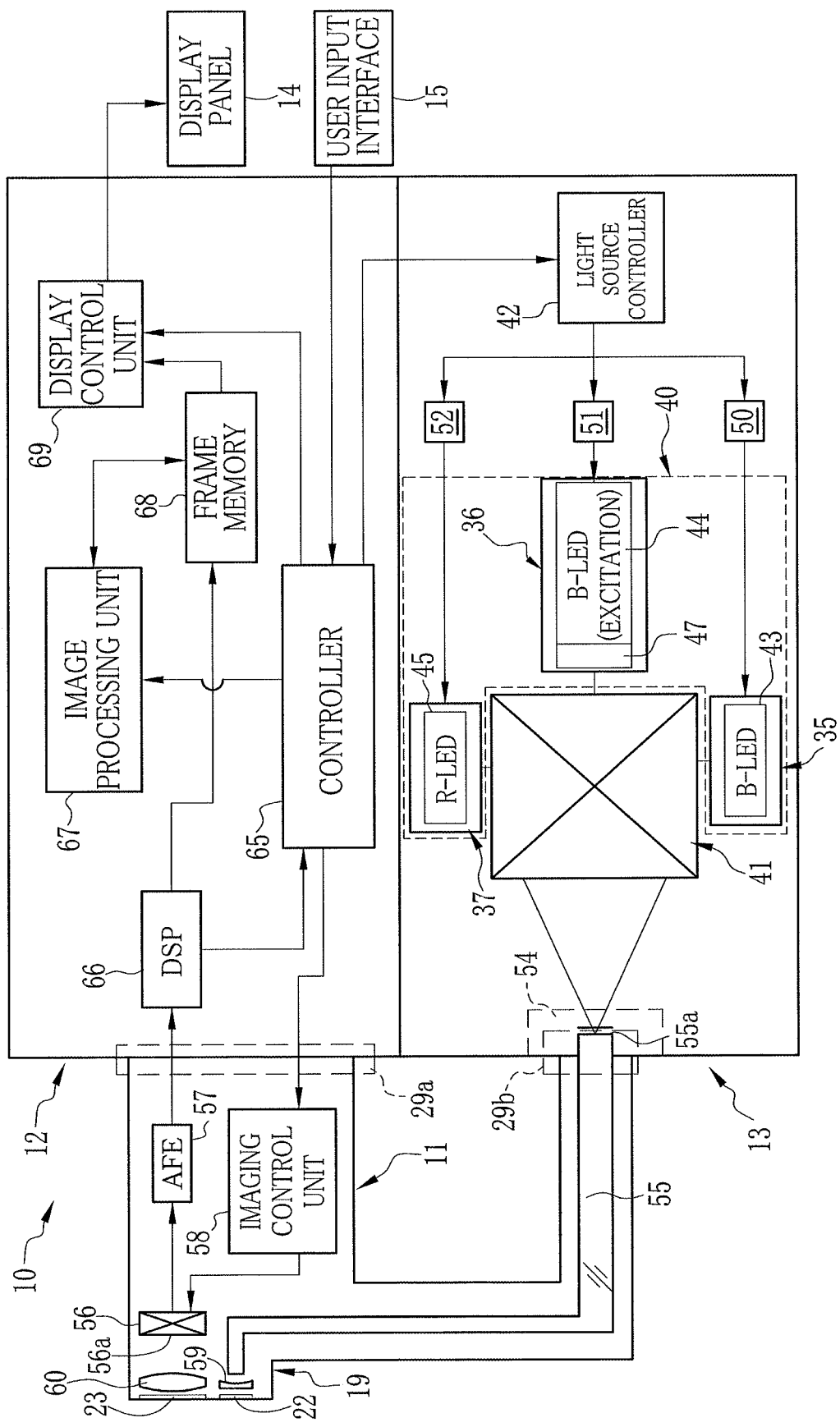
FIG. 3 is a block diagram schematically illustrating the endoscope system.

The steering device 20 is constituted by a plurality of link elements connected serially. Steering wheels 26 are disposed on the grip handle 17, and rotated to bend the steering device 20 up and down and to the right and left. The tip device 19 is directed in a desired direction by steering of the steering device 20. The flexible device 21 is flexible for entry in a body cavity of a tortuous shape, for example, esophagus or intestines in a gastrointestinal tract. A communication cable, a light guide device 55 and the like are extended through the elongated tube 16 as illustrated in FIG. 3. The communication cable transmits a drive signal for driving the image sensor 56, and an image signal output by the image sensor 56. The light guide device 55 transmits light from the light source apparatus 13 to the lighting windows 22.

The grip handle 17 includes a proximal instrument opening 27, fluid supply buttons 28 and a release button (not shown) in addition to the steering wheels 26. The proximal instrument opening 27 receives entry of a medical instrument for treatment. The fluid supply buttons 28 are depressed for supplying air or water through the nozzle spout 24. The release button is depressible for forming a still image.

A tube for the universal cable 18 contains the communication cable, the light guide device 55 and the like extending from the elongated tube 16. A composite connector 29 is disposed at a proximal end of the universal cable 18 on a side of the processing apparatus 12 and the light source apparatus 13. The composite connector 29 includes a cable connector plug 29a and a light source connector plug 29b. Those are coupled to respectively the processing apparatus 12 and the light source apparatus 13 in a removable manner. A proximal end of the communication cable is contained in the cable connector plug 29a. An entrance end 55a of the light guide device 55 of FIG. 3 is contained in the light source connector plug 29b.

In FIG. 3, the light source apparatus 13 includes a light source unit 40, a path coupler 41 and a light source controller 42. The light source unit 40 includes a blue light source 35, a fluorescent type of green light source 36 and a red light source 37 as semiconductor light sources. The path coupler 41 couples light paths of the B, G and R light sources 35-37 together. The light source controller 42 controls the B, G and R light sources 35-37.

The blue light source 35 includes a blue LED 43 (light emitting diode) for emitting light of a blue wavelength range. The red light source 37 includes a red LED 45 (light emitting diode) for emitting light of a red wavelength range. Furthermore, the green light source 36 includes a blue excitation light source device 44 or light source LED (light emitting diode), and green emitting phosphor 47. The blue excitation light source device 44 emits blue excitation light of a violet to blue wavelength range. The green emitting phosphor 47 is excited by the blue excitation light, and emits green fluorescence of a green wavelength range.

Each of the LEDs 43-45 has a p-type semiconductor and an n-type semiconductor attached together as is well-known in the art. Upon application of voltage, recombination of a positive hole and an electron occurs across the band gap at the p-n junction, for a current to flow. Light is emitted by generation of energy according to the band gap. A light amount emitted by the LEDs 43-45 is increased by an increase in supplied power. In the green light source 36 as a combination of the blue excitation light source device 44 and the green emitting phosphor 47, a light amount of the green fluorescence is increased by an increase in a light amount of the blue excitation light from the blue excitation light source device 44.

Figure 4:
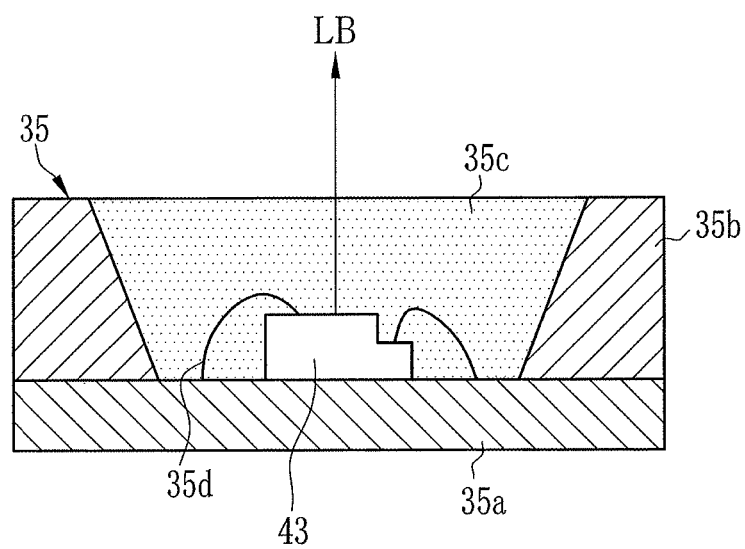
FIG. 4 is a cross section illustrating a blue semiconductor light source.

In FIG. 4, the blue light source 35 includes a semiconductor substrate 35a or semiconductor die, a cavity mold 35b and resin encapsulant 35c. On the semiconductor substrate 35a, the blue LED 43 is mounted. The cavity mold 35b is formed in the semiconductor substrate 35a, and has a cavity for containing the blue LED 43. The resin encapsulant 35c is filled in the cavity for encapsulation. An inner surface of the cavity is a reflector for reflecting light. Light diffusing material is mixed with and dispersed in the semiconductor substrate 35a for diffusing light. An LED wire 35d extends from the blue LED 43 to the semiconductor substrate 35a for connection with conductivity. In the technical field of the LED, this type of mounting of the blue light source 35 is referred to as a surface mounting type. Note that, in the red light source 37, the structure of the blue light source 35 is repeated. Details of the red light source 37 are not described herein.

Figure 5:
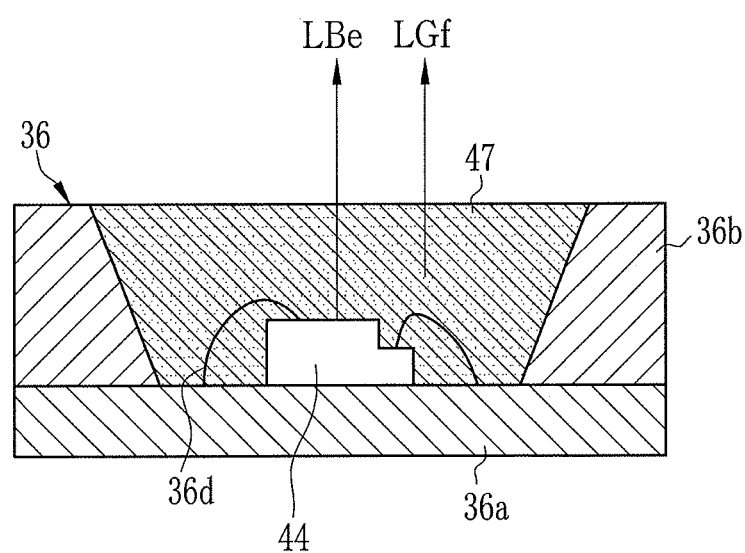
FIG. 5 is a cross section illustrating a green semiconductor light source.

In FIG. 5, the green light source 36 of the fluorescent type includes a semiconductor substrate 36a or semiconductor die, and a cavity mold 36b, and is packaged with the blue excitation light source device 44 in the surface mounting type, in a manner similar to the blue and red light sources 35 and 37. The green light source 36 is different from the blue and red light sources 35 and 37 in that the green emitting phosphor 47 is contained in the cavity of the cavity mold 36b. The green emitting phosphor 47 in the blue excitation light source device 44 is dispersed in resin encapsulant, and includes dispersed materials such as phosphor, light diffusing material and the like. An LED wire 36d is disposed to connect the semiconductor substrate 36a to the blue excitation light source device 44.

Figure 6:
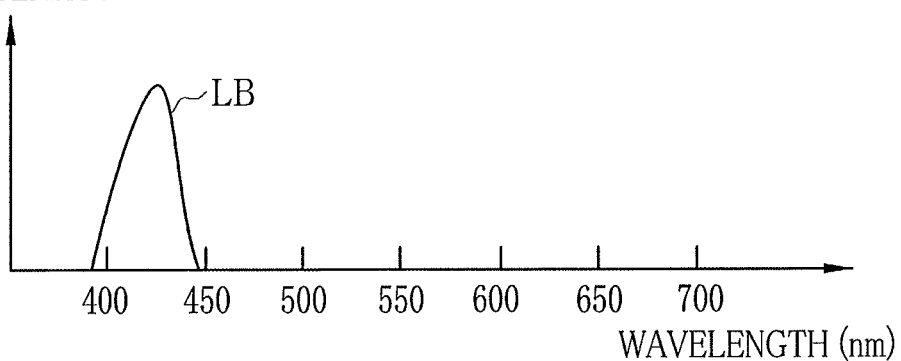
FIG. 6 is a graph illustrating a spectrum of light from the blue light source.
Figure 7:
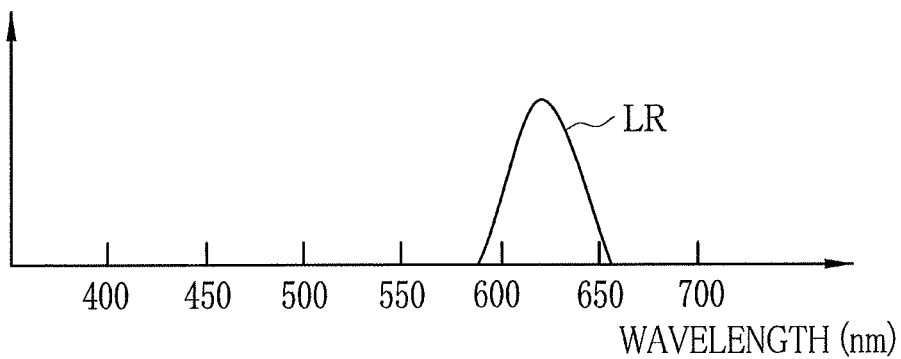
FIG. 7 is a graph illustrating a spectrum of light from a red semiconductor light source.

In FIG. 6, the blue LED 43 emits blue light LB of which a wavelength range is 390-445 nm of violet to blue colors, and a peak wavelength is 430 plus or minus 10 nm. In FIG. 7, the red LED 45 emits red light LR of which a wavelength range is 615-635 nm of a red color, and a peak wavelength is 620 plus or minus 10 nm.

Figure 8:
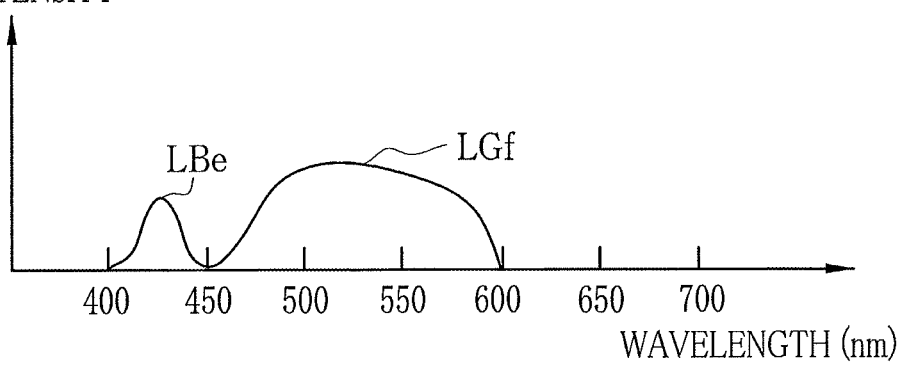
FIG. 8 is a graph illustrating spectra of blue excitation light and green fluorescence of the green light source.

In FIG. 8, the green light source 36 emits mixed light (LBe+LGf) of blue excitation light LBe from the blue excitation light source device 44 and green fluorescence LGf emitted by the green emitting phosphor 47 excited by the blue excitation light LBe. The blue excitation light LBe has a violet to blue wavelength range of 420-440 nm and a peak wavelength of 430 plus or minus 10 nm. The green fluorescence LGf has a green wavelength range of 500-600 nm and a peak wavelength of 520 plus or minus 10 mm. The peak wavelength of the blue excitation light LBe is equal to that of the blue light LB emitted by the blue light source 35. The wavelength range of the blue excitation light LBe is overlapped with that of the blue light LB. See FIG. 19.

The green emitting phosphor 47 absorbs a large part of the blue excitation light LBe to emit the green fluorescence LGf. A remaining part of the blue excitation light LBe passes the green emitting phosphor 47 without absorption. A spectrum of light emitted by the green light source 36, as illustrated in the drawing, contains a component of the passed part of the blue excitation light LBe through the green emitting phosphor 47 and a component of the green fluorescence LGf.

Figure 9:
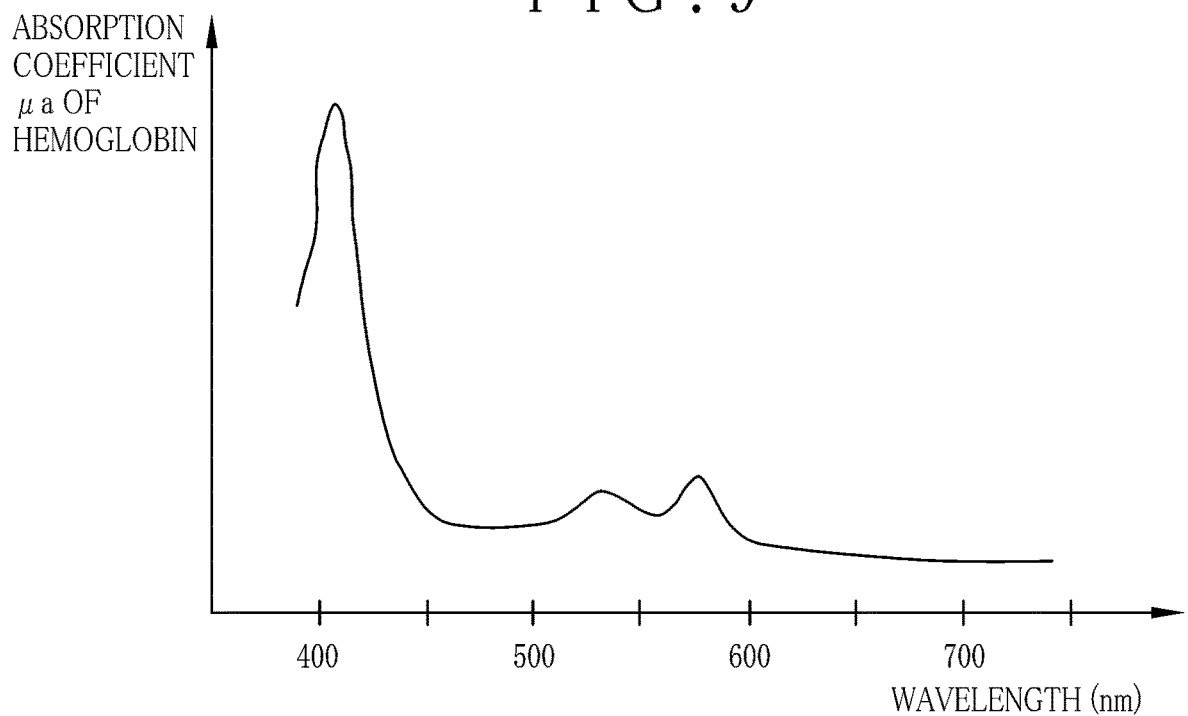
FIG. 9 is a graph illustrating an absorption spectrum of hemoglobin.

In FIG. 9, an absorption spectrum of hemoglobin in blood is illustrated. An absorption coefficient μm has dependency to the wavelength, namely increases abruptly in a wavelength range equal to or lower than 450 nm, and comes to a peak at approximately 405 nm. Also, the absorption coefficient comes to a smaller peak at a wavelength of 530-560 nm. In case light of a wavelength range with a high value of the absorption coefficient μa is applied to body tissue or an object of interest, an image with a difference in the contrast between blood vessels and other tissue can be obtained, because the light is largely absorbed by the blood vessels.

Figure 10:
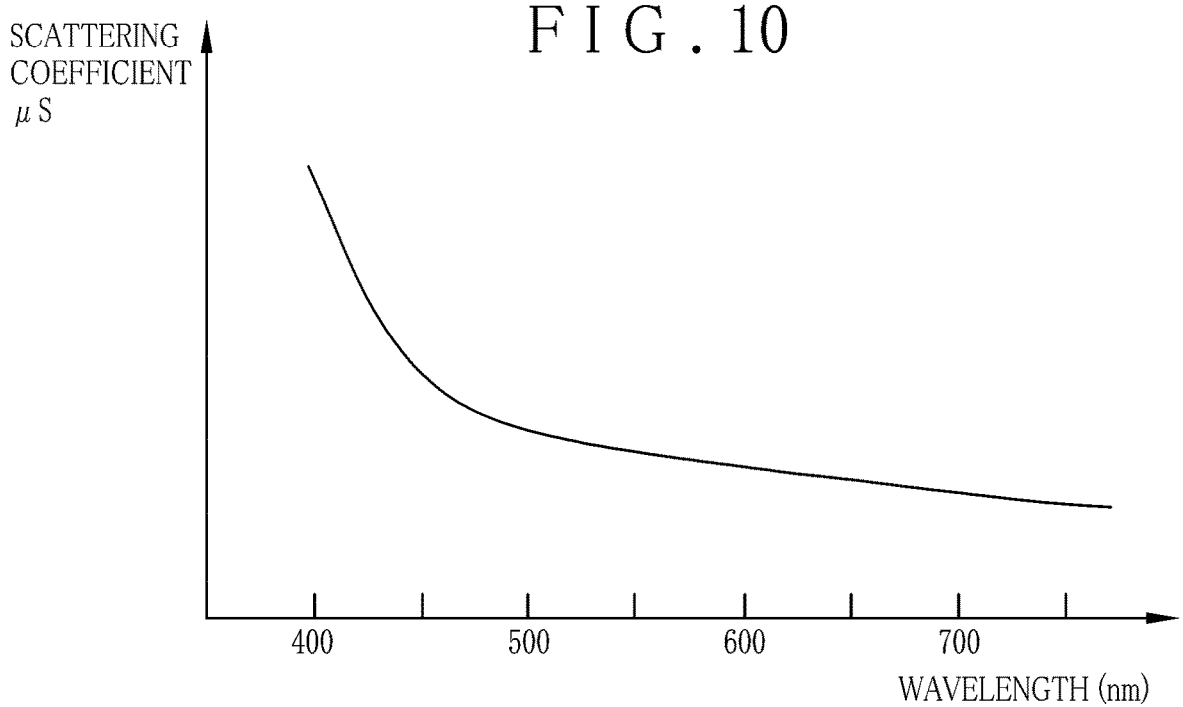
FIG. 10 is a graph illustrating a scattering coefficient of body tissue.

In FIG. 10, a scattering characteristic of body tissue to light also has dependency to the wavelength. A scattering coefficient μS increases according to smallness of the wavelength. The scattering influences a depth of penetration of light into the body tissue. An amount of light reflected in the vicinity of the epithelium (mucosa surface) of the body tissue is high according to highness of the scattering, so as to decrease an amount of light reaching a portion of a medium depth or large depth (lamina propria or muscularis mucosae). Accordingly, the depth of penetration decreases according to the smallness of the wavelength, and increases according to greatness of the wavelength. A wavelength of light for the vessel enhancement is selected according to the absorption characteristic of hemoglobin and scattering characteristic of body tissue to light.

The blue light LB with the peak wavelength of 430 plus or minus 10 nm from the blue LED 43 has a relatively small depth of penetration with a relatively short wavelength. Absorption of the blue light LB in surface blood vessels is large. Thus, the blue light LB is used for enhancement of surface blood vessels. It is possible to obtain a vessel enhancement image in which surface blood vessels are expressed with high contrast by use of the blue light LB. Also, green fluorescence LGf with the peak wavelength of 520 plus or minus 10 nm is used for enhancement of subsurface or deep blood vessels. In FIG. 9 for the absorption spectrum, the absorption coefficient changes gradually in a green wavelength range of 530-560 nm in comparison with a blue wavelength range equal to or less than 450 nm. There is no requirement of narrow band light for the purpose of enhancement of subsurface or deep blood vessels in a manner different from the blue light LB. Thus, a green image signal after color separation with a micro color filter of green in the image sensor 56 is used for enhancement of the subsurface or deep blood vessels, as will be described later. In FIG. 3, drivers 50, 51 and 52 are connected to respectively the LEDs 43-45. The light source controller 42 controls the drivers 50-52 to turn on and off the LEDs 43-45 and adjust their light amounts. According to an exposure control signal from the processing apparatus 12, the light source controller 42 adjusts the light amounts by changing power supplied to the LEDs 43-45.

The drivers 50-52 are controlled by the light source controller 42, and turn on respectively the LEDs 43-45 by application of drive currents. In response to the exposure control signal from the processing apparatus 12, the drivers 50-52 change the current values to adjust power for the LEDs 43-45, so that light amounts of the blue light LB, green fluorescence LGf and red light LR are controlled. Control of the light amount of the green fluorescence LGf is performed by controlling a light amount of the blue excitation light LBe from the blue excitation light source device 44. In case an operator wishes an increase of the light amount of the green fluorescence LGf, the current value from the driver 51 to the blue excitation light source device 44 is increased to increase the light amount of the blue excitation light LBe. Note that various methods of supplying a drive current can be used, such as controls of PAM (pulse amplitude modulation) and PWM (pulse width modulation). In the PAM, an amplitude of a pulse of the drive current is changed. In the PWM, a duty factor of the pulse of the drive current is changed.

The path coupler 41 couples light paths of light from the B, G and R light sources 35-37 together into one light path. There is a receptacle connector 54 for connection of the light source connector plug 29b. A distal end of the path coupler 41 is disposed near to the receptacle connector 54. The path coupler 41 receives the light from the B, G and R light sources 35-37 and outputs the light toward the entrance end 55a of the light guide device 55 in the endoscope 11. Protectors (not shown) of glass are associated with respectively the light source connector plug 29b and the receptacle connector 54.

Figure 11:
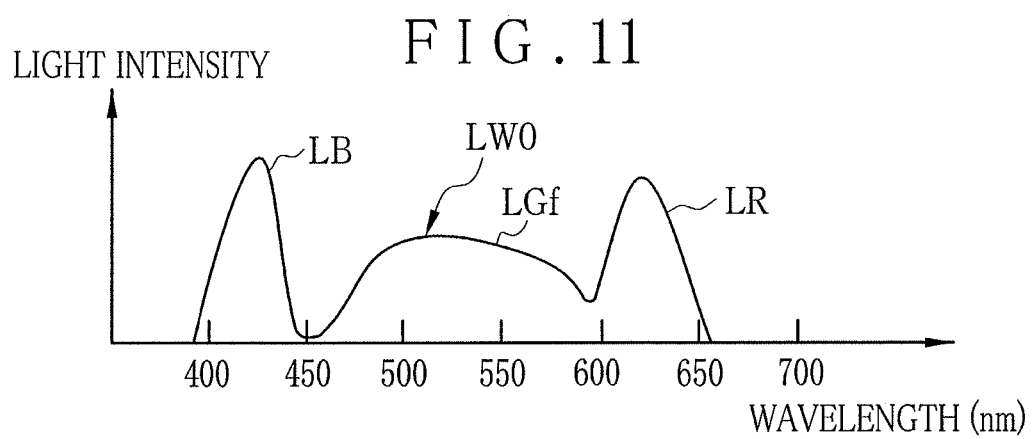
FIG. 11 is a graph illustrating a spectrum of illumination light containing the blue light, green fluorescence and red light.
Figure 12:
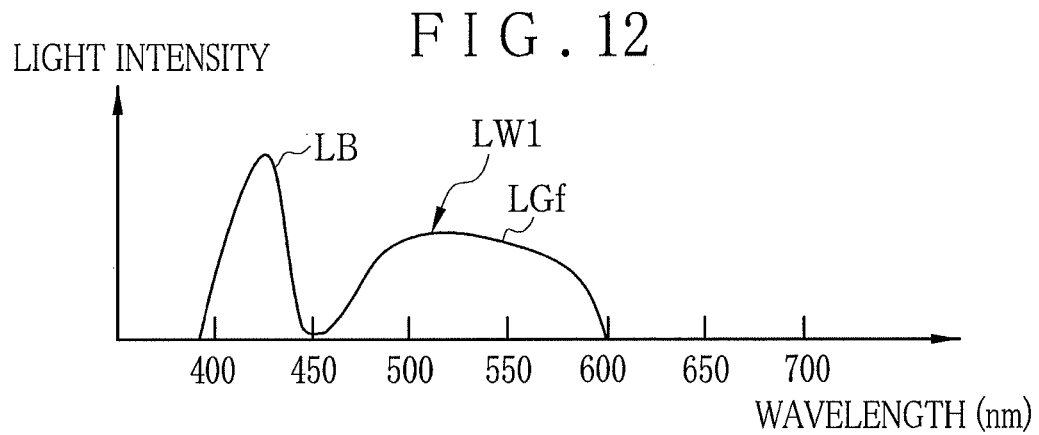
FIG. 12 is a graph illustrating a spectrum of illumination light containing the blue light and green fluorescence.

In FIG. 11, a spectrum of mixed light of the blue light LB, green fluorescence LGf and red light LR from the B, G and R light sources 35-37 at a point downstream of the path coupler 41 is illustrated. The mixed light is white light with the continuous spectrum fully extending in a visible light range, and used as illumination light LW0 in the normal imaging mode. In the vessel enhancement imaging mode, illumination light LW1 is applied to an object of interest as mixed light of the blue light LB and green fluorescence LGf. See FIG. 12. A second dichroic mirror 80 of FIG. 18 cuts off the blue excitation light LBe, so that no component of the blue excitation light LBe is contained in a spectrum of the illumination light LW0 and LW1. Note that the spectra of the illumination light LW0 and LW1 in FIGS. 11 and 12 are only examples. Spectra of the illumination light LW0 and LW1 can be changed suitably as target according to color balance of a display image or the like. For example, a ratio between light amounts of the blue light LB, green fluorescence LGf and red light LR (ratio between current values of drive currents for the LEDs 43-45) is adjusted to produce the illumination light LW0 and LW1 with a spectrum of the target.

The light source controller 42 controls the exposure of the light of illumination by maintaining the spectrum of light emission as a target. Should a ratio of light amounts of the colors be changed within the light of illumination, color balance of a display image may change with a change in the spectrum of the light emission. Thus, the light source controller 42 discretely changes a current value of driving the LEDs 43-45 by controlling the drivers 50-52, to increase or decrease the light amounts of the colors.

The light source controller 42 changes the spectrum of light between the normal imaging mode and the vessel enhancement imaging mode. For example, the light source controller 42 sets the ratio of the light amount of the blue light LB higher in the vessel enhancement imaging mode than in the normal imaging mode, so as to use the blue light LB with higher importance than the green fluorescence LGf.

In FIG. 3, the endoscope 11 includes the light guide device 55, the image sensor 56, an analog processing unit 57 or analog front end (AFE), and an imaging control unit 58. The light guide device 55 is a fiber bundle constituted by bundling plural optical fibers. Upon coupling the light source connector plug 29b to the light source apparatus 13, the entrance end 55a of the light guide device 55 in the light source connector plug 29b is aligned with an exit end of the path coupler 41. A distal exit end of the light guide device 55 inside the tip device 19 has two branches for transmitting light to the lighting windows 22.

A lighting lens 59 is disposed behind each of the lighting windows 22. Illumination light from the light source apparatus 13 is guided by the light guide device 55 to the lighting lens 59, and applied through the lighting windows 22 to an object of interest. The lighting lens 59 is a concave lens and enlarges a divergence angle of light from the light guide device 55. The illumination light can be applied to a wide area in a body cavity with the object of interest.

The objective lens 60 and the image sensor 56 are disposed behind the viewing window 23. Image light from the object of interest enters the objective lens 60 through the viewing window 23, and is focused on an imaging surface 56a of the image sensor 56 by the objective lens 60.

Examples of the image sensor 56 are a CCD image sensor and CMOS image sensor. A plurality of photoconductive elements or photoconductors are arranged as pixels of arrays on the imaging surface 56a, for example, photo diodes. The image sensor 56 photoelectrically converts light received by the imaging surface 56a, and stores signal charge according to light amounts of light received by the pixels. The signal charge is converted by an amplifier into a voltage signal, which is read out. The voltage signal is transmitted by the image sensor 56 to the analog processing unit 57 as an image signal.

The analog processing unit 57 is constituted by a correlated double sampler (CDS), auto gain controller (AGC) and A/D converter (all not shown). The correlated double sampler processes the image signal of an analog form from the image sensor 56 in the correlated double sampling, and removes electric noise due to reset of the signal charge. The auto gain controller amplifies the image signal after removal of the noise in the correlated double sampler. The A/D converter converts the amplified image signal from the auto gain controller into a digital image signal having a gradation value according to a predetermined bit number, and sends the digital image signal to the processing apparatus 12.

A controller 65 in the processing apparatus 12 is connected with the imaging control unit 58, which supplies the image sensor 56 with a drive signal according to a clock signal from the controller 65 as a reference. The image sensor 56 generates an image signal at a predetermined frame rate according to the drive signal from the imaging control unit 58, and sends the image signal to the analog processing unit 57.

Figure 13:
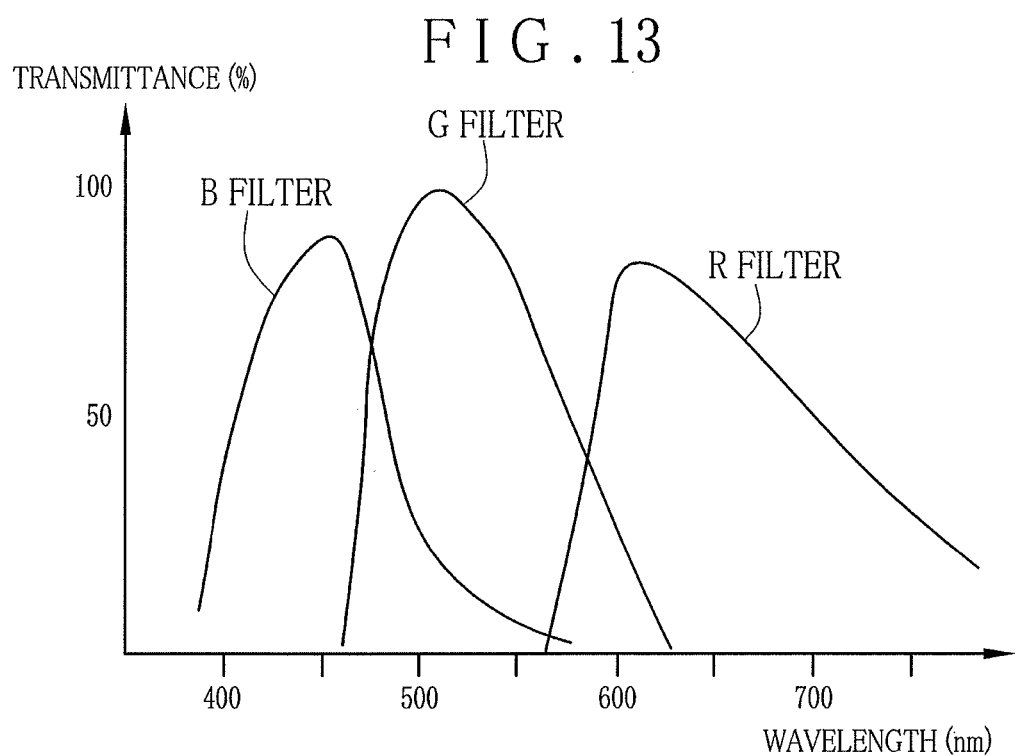
FIG. 13 is a graph illustrating a spectral characteristic of micro color filters.

The image sensor 56 is a color image sensor. The imaging surface 56a of the image sensor 56 has a great number of micro color filters of blue, green and red with spectral characteristics in FIG. 13 in correspondence with pixels. An example of arrangement of the micro color filters is a Bayer arrangement.

The B pixels with the B filters are sensitive to light of a wavelength of approximately 380-560 nm. The G pixels with the G filters are sensitive to light of a wavelength of approximately 450-630 nm. The R pixels with the R filters are sensitive to light of a wavelength of approximately 580-800 nm. Reflected light corresponding to the blue light LB is mainly received by the B pixels. Reflected light corresponding to the green fluorescence LGf is mainly received by the G pixels. Reflected light corresponding to the red light LR is mainly received by the R pixels. The blue excitation light LBe does not travel to the object of interest because cut off by the second dichroic mirror 80. Assuming that the blue excitation light LBe illuminates the object, reflected light from the object is sensed by the B pixels.

Figure 14:
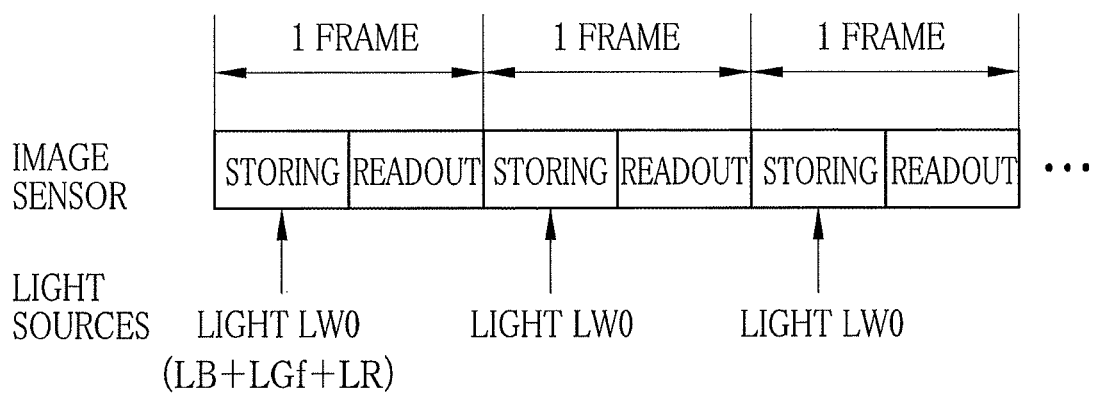
FIG. 14 is a timing chart illustrating lighting and imaging according to normal imaging.
Figure 15:
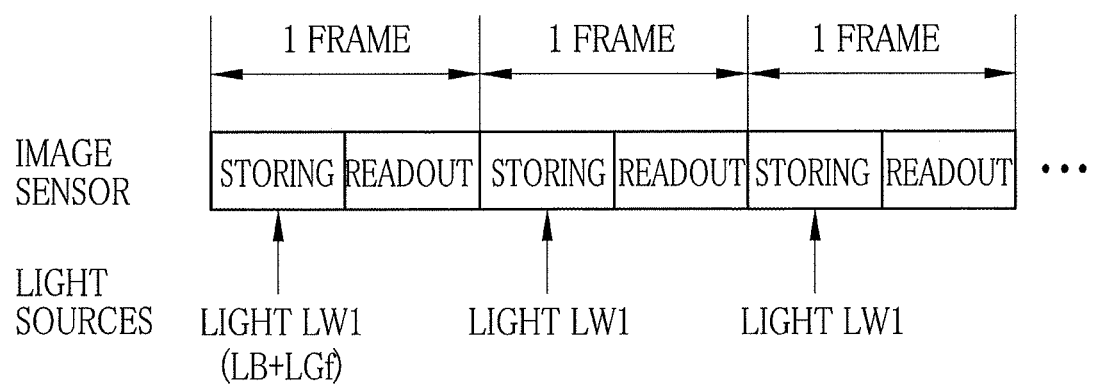
FIG. 15 is a timing chart illustrating lighting and imaging according to vessel enhancement imaging.

In FIGS. 14 and 15, the image sensor 56 operates for the storing and readout in a period of acquiring one frame, and in the storing, stores signal charge in pixels, and in the readout, reads out the stored signal charge. In FIG. 14, the B, G and R light sources 35-37 in the normal imaging mode are turned on according to a time point of the storing of the image sensor 56, to apply the illumination light LW0 (LB+LGf+LR) to an object of interest, the illumination light LW0 being mixture of the blue light LB, green fluorescence LGf and red light LR. Object light or reflected light becomes incident upon the image sensor 56. The image sensor 56 separates the reflected light of the illumination light LW0 with the micro color filter. Blue pixels receive reflected light derived from the blue light LB. Green pixels receive reflected light derived from the green fluorescence LGf. Red pixels receive reflected light derived from the red light LR. The image sensor 56 sequentially outputs image signals B, G and R of one frame according to pixel values of the blue, green and red pixels at a time point of the readout and with the frame rate. The imaging sequence is repeated while the normal imaging mode is set.

In FIG. 15, the blue and green light sources 35 and 36 in the vessel enhancement imaging mode are turned on according to a time point of the storing of the image sensor 56, to apply illumination light LW1 (LB+LGf) to the object of interest, the illumination light LW1 being mixture of the blue light LB and green fluorescence LGf.

The illumination light LW1 is separated by the micro color filters in the image sensor 56 in a manner similar to the normal imaging mode. The B and G pixels receive reflected light derived from the blue light LB and from the green fluorescence LGf in a manner similar to the normal imaging mode. The image sensor 56 outputs image signals B, G and R sequentially in a sequence of readout in the vessel enhancement imaging mode. Those steps of the imaging are repeated while the vessel enhancement imaging mode is set.

In FIG. 3, the processing apparatus 12 includes a digital signal processor 66 (DSP), an image processing unit 67, a frame memory 68 and a display control unit 69 together with the controller 65. The controller 65 has a CPU with a ROM and a RAM. The ROM stores control programs and control data. The RAM is a working memory for loading of the control programs. The CPU runs the control programs to control various elements in the processing apparatus 12.

The digital signal processor 66 acquires an image signal output by the image sensor 56. The digital signal processor 66 separates the image signal of the mixture for blue, green and red pixels into image signals of blue, green and red. The image signals of the colors are interpolated in the operation of pixel interpolation. The digital signal processor 66 performs signal processing of various functions, such as gamma correction, white balance correction and the like for the image signals of blue, green and red.

The digital signal processor 66 determines an exposure amount according to the image signals B, G and R. Should the exposure amount of the entirety of the image be too low (underexposure), the digital signal processor 66 outputs a control signal to the controller 65 to raise the light amount of the illumination light. Should the exposure amount of the entirety of the image be too high (overexposure), the digital signal processor 66 outputs a control signal to the controller 65 to lower the light amount of the illumination light. The controller 65 sends the control signal to the light source controller 42 of the light source apparatus 13.

The frame memory 68 stores image data output by the digital signal processor 66, processed image data from the image processing unit 67, and the like. The display control unit 69 reads out the processed image data from the frame memory 68, converts this into a video signal such as a composite signal, component signal or the like, which is output to the display panel 14.

Figure 16:
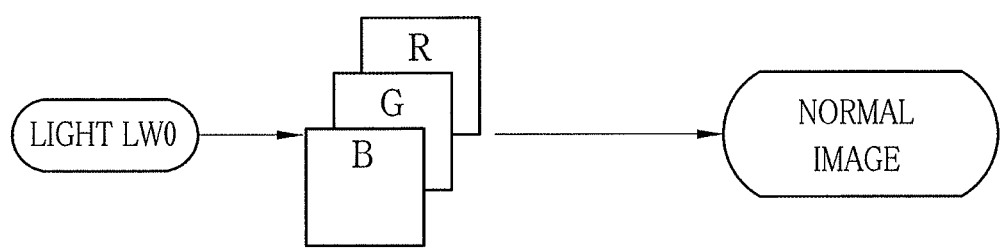
FIG. 16 is a flow chart illustrating image processing in the normal imaging.

In FIG. 16, the image processing unit 67 in the normal imaging mode generates a normal image according to the image signals B, G and R after color separation by the digital signal processor 66. The normal image is output to the display panel 14. The image processing unit 67 updates the normal image at each time that the image signals B, G and R in the frame memory 68 are updated.

Figure 17:
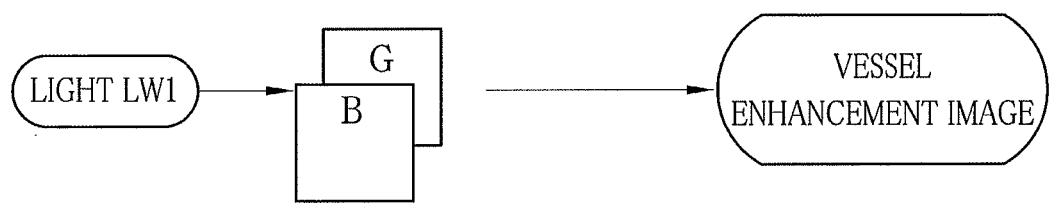
FIG. 17 is a flow chart illustrating image processing in the vessel enhancement imaging.

In FIG. 17, the image processing unit 67 generates a vessel enhancement image according to image signals B and G in the vessel enhancement imaging mode. The image signal B in the vessel enhancement imaging mode includes a component of reflected light derived from the blue light LB having a wavelength of 390-445 nm and a peak wavelength of 430 plus or minus 10 nm. Thus, the surface blood vessels can be expressed at a high contrast. It is medically known that there is a characteristic pattern of the particular surface blood vessels in body tissue of a cancer, malignant tumor or other lesions, because higher vessel density of the particular surface blood vessels is found than normal body tissue. It is preferable to express the particular surface blood vessels distinctly with advantages for the diagnosis of a benign or malignant tumor.

It is also possible to extract an area of the surface blood vessels within the endoscopic image according to the image signal B, and process the area of the surface blood vessels in edge enhancement as processing well-known in the art. The image signal B after the edge enhancement is combined with the image signal G, to produce a vessel enhancement image. Also, an area of subsurface or deep blood vessels can be processed in the edge enhancement in addition to the surface blood vessels. To this end, an area of the subsurface or deep blood vessels is extracted from the image signal G containing much information of the subsurface or deep blood vessels, and is processed in the edge enhancement. A vessel enhancement image is produced according to the image signal G after the edge enhancement and the image signal B.

The image processing unit 67 generates the vessel enhancement image at each time that the image signals B and G in the frame memory 68 are updated. The display control unit 69 allocates the image signal B to the B and G channels of the display panel 14, and the image signal G to the R channel of the display panel 14, and drives the display panel 14 to display the vessel enhancement image in a form of pseudo color.

Figure 18:
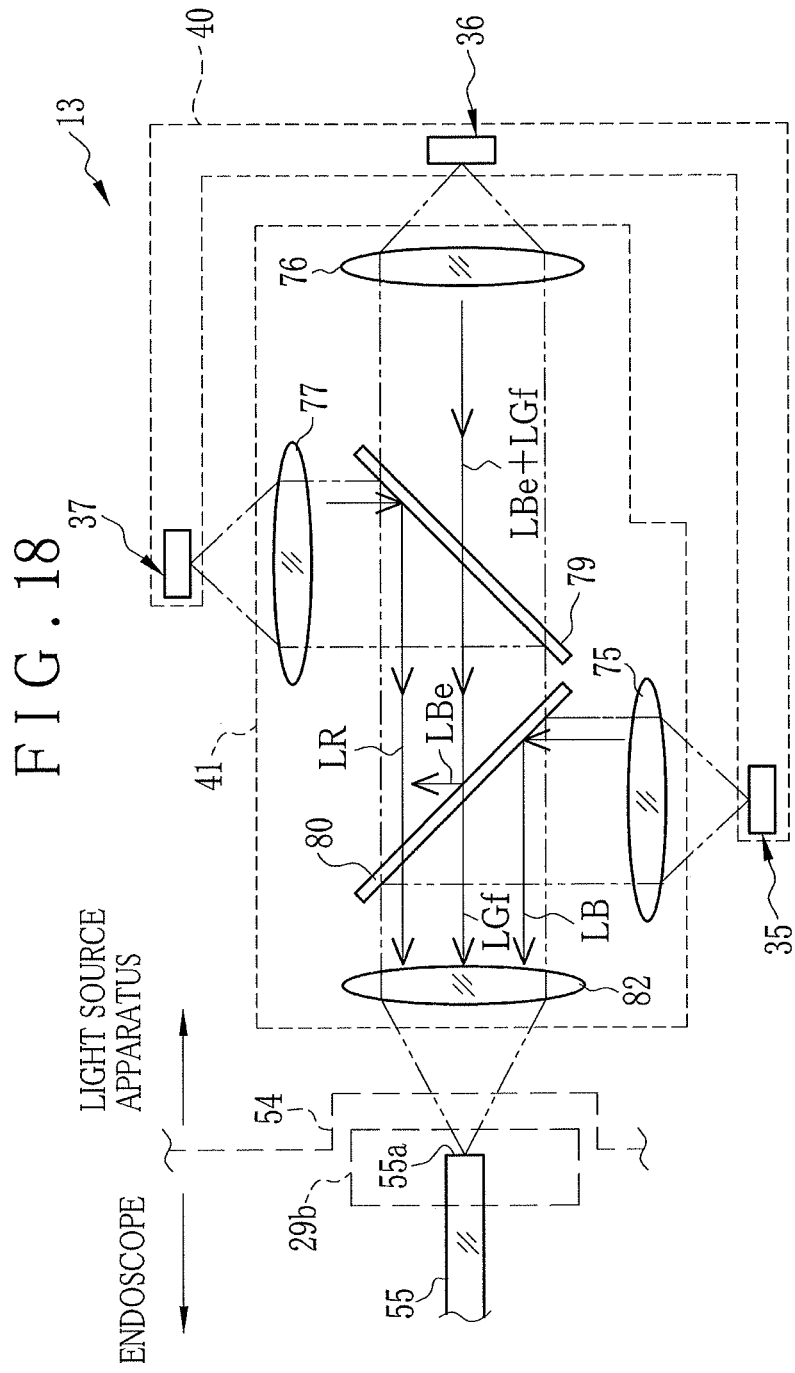
FIG. 18 is an explanatory view in a side elevation illustrating the light sources and a path coupler.

In FIG. 18, the path coupler 41 includes collimator lenses 75, 76 and 77, a first dichroic mirror 79, the second dichroic mirror 80 and a condenser lens 82. The collimator lenses 75-77 collimate light of the colors from respectively the B, G and R light sources 35-37. The condenser lens 82 condenses light from the path coupler 41 to the entrance end 55a of the light guide device 55. Each of the first and second dichroic mirrors 79 and 80 is optics including a transparent glass plate and a layer of a dichroic filter formed on the glass plate with a predetermined transmission characteristic.

The green light source 36 is so disposed that its light path is aligned with an optical axis of the light guide device 55. The light paths of the green and red light sources 36 and 37 are perpendicular with one another. The first dichroic mirror 79 is positioned at a point of the intersection between the light paths of the green and red light sources 36 and 37. Also, the light paths of the blue and green light sources 35 and 36 are perpendicular with one another. The second dichroic mirror 80 is positioned at a point of the intersection between the light paths of the blue and green light sources 35 and 36. The first dichroic mirror 79 is oriented with an inclination of 45 degrees with respect to the light paths of the green and red light sources 36 and 37. The second dichroic mirror 80 is oriented with an inclination of 45 degrees with respect to the light paths of the blue and green light sources 35 and 36.

Figure 19:
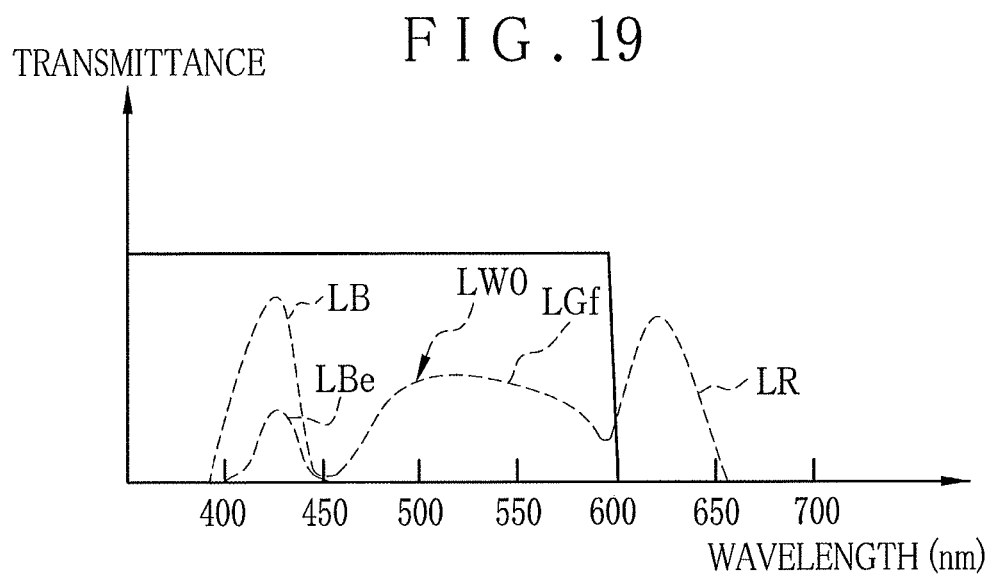
FIG. 19 is a graph illustrating a transmission characteristic of a dichroic filter in a first dichroic mirror.

In FIG. 19, the dichroic filter of the first dichroic mirror 79 has a transmission characteristic of reflecting light of a red wavelength range equal to or more than approximately 600 nm and passing light of a blue to green wavelength range less than the same. The first dichroic mirror 79 passes the mixed light of the blue excitation light LBe and green fluorescence LGf from the green light source 36 through the collimator lens 76, and reflects the red light LR from the red light source 37 through the collimator lens 77. Thus, a light path of the mixed light of the blue excitation light LBe and green fluorescence LGf is combined with that of the red light LR for coupling.

A dichroic filter in the second dichroic mirror 80 has a transmission characteristic of cutting off at least the blue excitation light LBe from a spectrum of mixed light of the blue excitation light LBe and green fluorescence LGf downstream of the green light source 36 as illustrated in FIG. 8. In short, the dichroic filter in the second dichroic mirror 80 operates as an excitation light cut-off filter (wavelength cut-off filter component) for cutting off the blue excitation light LBe.

Figure 20:
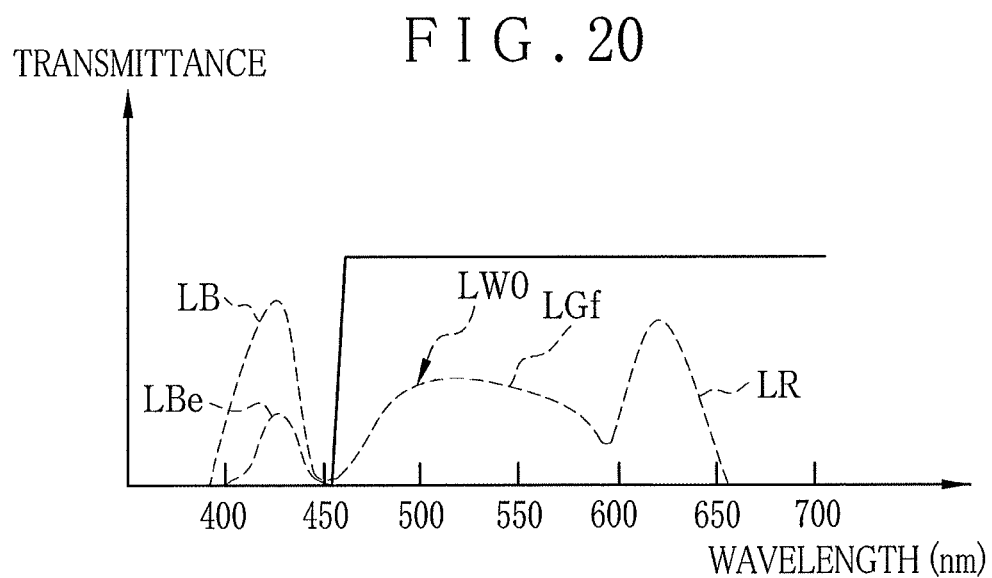
FIG. 20 is a graph illustrating a transmission characteristic of a dichroic filter in a second dichroic mirror.

In FIG. 20, the dichroic filter of the second dichroic mirror 80 has a transmission characteristic of reflecting light of a violet to blue wavelength range less than approximately 460 nm and passing light of a green to red wavelength range more than the same. The second dichroic mirror 80 reflects the blue excitation light LBe in the mixed light of the blue excitation light LBe and green fluorescence LGf downstream of the first dichroic mirror 79, and passes the green fluorescence LGf. Also, the second dichroic mirror 80 passes the red light LR reflected by the first dichroic mirror 79, and reflects the blue light LB from the blue light source 35 through the collimator lens 75. Thus, the second dichroic mirror 80 couples light paths of the blue excitation light LBe, green fluorescence LGf and red light LR together. Note that the blue excitation light LBe does not enter the entrance end 55a of the light guide device 55, and is prevented from illuminating an object of interest.

The operation of the present embodiment is described now. For endoscopic imaging, the endoscope 11 is connected to the processing apparatus 12 and the light source apparatus 13. A power source for the processing apparatus 12 and the light source apparatus 13 is turned on to start up the endoscope system 10.

The elongated tube 16 of the endoscope 11 is entered in the gastrointestinal tract of the patient to start imaging. In the normal imaging mode, the B, G and R light sources 35-37 are turned on. The light source controller 42 sets current values for driving the LEDs 43-45 at a level suitable for the normal imaging mode, and starts driving the B, G and R light sources 35-37. The light source controller 42 controls light amounts by maintaining a spectrum of emission for a target.

In the blue and red light sources 35 and 37, the LEDs 43 and 45 emit blue light LB and red light LR. The green light source 36 of the fluorescent type emits mixed light of the blue excitation light LBe from the blue excitation light source device 44 and the green fluorescence LGf from the green emitting phosphor 47 upon excitation with the blue excitation light LBe. The components of the light enter the collimator lenses 75-77 in the path coupler 41.

The red light LR is reflected by the first dichroic mirror 79 and passed through the second dichroic mirror 80. The mixed light of the blue excitation light LBe and green fluorescence LGf is passed through the first dichroic mirror 79. The blue excitation light LBe is reflected by the second dichroic mirror 80. The green fluorescence LGf is passed through the second dichroic mirror 80. Thus, the first dichroic mirror 79 couples light paths of the red light LR, the blue excitation light LBe and the green fluorescence LGf in mixture. The second dichroic mirror 80 cuts off the blue excitation light LBe. The dichroic filter in the second dichroic mirror 80 operates as an excitation light cut-off filter (wavelength cut-off filter component), so that the optical system of the path coupler 41 can be constructed with simplicity.

The blue light LB is reflected by the second dichroic mirror 80. The second dichroic mirror 80 couples the paths of the blue light LB, green fluorescence LGf and red light LR together. The light components of the blue light LB, green fluorescence LGf and red light LR become incident upon the condenser lens 82. Thus, illumination light LW0 is produced from the combination of the blue light LB, green fluorescence LGf and red light LR. The condenser lens 82 condenses the illumination light LW0 at the entrance end 55a of the light guide device 55 of the endoscope 11, and supplies the endoscope 11 with the illumination light LW0.

In the endoscope 11, the illumination light LW0 is guided through the light guide device 55 to the lighting windows 22, and applied to an object of interest. Reflected light of the illumination light LW0 from the object of interest becomes incident upon the image sensor 56 through the viewing window 23. The image sensor 56 outputs image signals B, G and R to the digital signal processor 66 of the processing apparatus 12. The digital signal processor 66 separates the image signals B, G and R by color separation, and inputs those to the image processing unit 67. Imaging of the image sensor 56 is repeated at a predetermined frame rate. The image processing unit 67 generates a normal image according to the image signals B, G and R. The display control unit 69 outputs the normal image to the display panel 14. Also, the normal image is updated according to the frame rate of the image sensor 56.

The digital signal processor 66 obtains an exposure amount according to the image signals B, G and R, and transmits an exposure control signal to the light source controller 42 of the light source apparatus 13 according to the obtained exposure amount. The light source controller 42 acquires current values of driving the B, G and R light sources 35-37 according to the exposure control signal so as to keep a constant ratio between the light amounts of the colors (or not to change the spectrum of the light emission of a target). Thus, the B, G and R light sources 35-37 are driven according to the acquired current values. It is therefore possible to keep the light amounts of the blue light LB, green fluorescence LGf and red light LR from the B, G and R light sources 35-37 at the constant ratio suitable for the normal imaging mode.

To change the light amount of green fluorescence LGf in the exposure control, the light amount of blue excitation light LBe from the blue excitation light source device 44 is changed. In FIG. 19, a wavelength range of the blue excitation light LBe overlaps on that of the blue light LB. Assuming that the blue excitation light LBe is emitted for illumination, a light amount of the blue light LB is also changed by a change in that of the blue excitation light LBe. The spectrum of the light is changed. However, the second dichroic mirror 80 cuts off the blue excitation light LBe, so that the light amount of the blue light LB is controlled discretely from the green fluorescence LGf without influence of the blue excitation light LBe to the light amount of the blue light LB. Consequently, the endoscope 11 can be supplied with light of the spectrum appropriate for the normal imaging mode even upon performing the exposure control. No change occurs in the color balance of the normal image.

Assuming that an object with appearance of a lesion is discovered in the normal imaging mode, the imaging mode is changed over to the vessel enhancement imaging mode. The red light source 37 is turned off, and the blue and green light sources 35 and 36 are turned on. Color light from the blue and green light sources 35 and 36 is combined to become the illumination light LW1 by the path coupler 41, and is supplied to the endoscope 11. In a manner similar to the normal imaging mode, the second dichroic mirror 80 cuts off the blue excitation light LBe. Thus, the endoscope 11 can be supplied constantly with light of a spectrum suitable for the vessel enhancement imaging mode, without change in the color balance of a vessel enhancement image.

The image sensor 56 receives reflected light from an object of interest illuminated by the illumination light LW1, and outputs image signals B, G and R to the digital signal processor 66. The digital signal processor 66 separates the image signals B, G and R and inputs those to the image processing unit 67, which generates a vessel enhancement image according to the image signals B and G. The vessel enhancement image is output to the display panel 14. This image is updated according to the frame rate of the image sensor 56.

Therefore, reliability of a vessel enhancement image can be high owing to constant emission of light of a spectrum suitable of the vessel enhancement imaging. The vessel enhancement image is used for diagnosing a benign or malignant tumor. Reliability in the diagnosis of a tumor can be high according to the highness in the reliability in the vessel enhancement image.

The blue excitation light LBe with influence to the light amount of the blue light LB is cut off by the second dichroic mirror 80. Thus, it is possible to supply light of illumination with the spectrum of target without complicated control of adjusting the light amount of the blue light LB and the like in consideration of a change in the blue excitation light LBe with a change in the green fluorescence LGf.

Second Preferred Embodiment

In the first embodiment, the second dichroic mirror 80 includes the dichroic filter functioning as an excitation light cut-off filter. In the second embodiment, a dichroic mirror separate from the second dichroic mirror 80 has a dichroic filter functioning as an excitation light cut-off filter (wavelength cut-off filter component).

Figure 21:
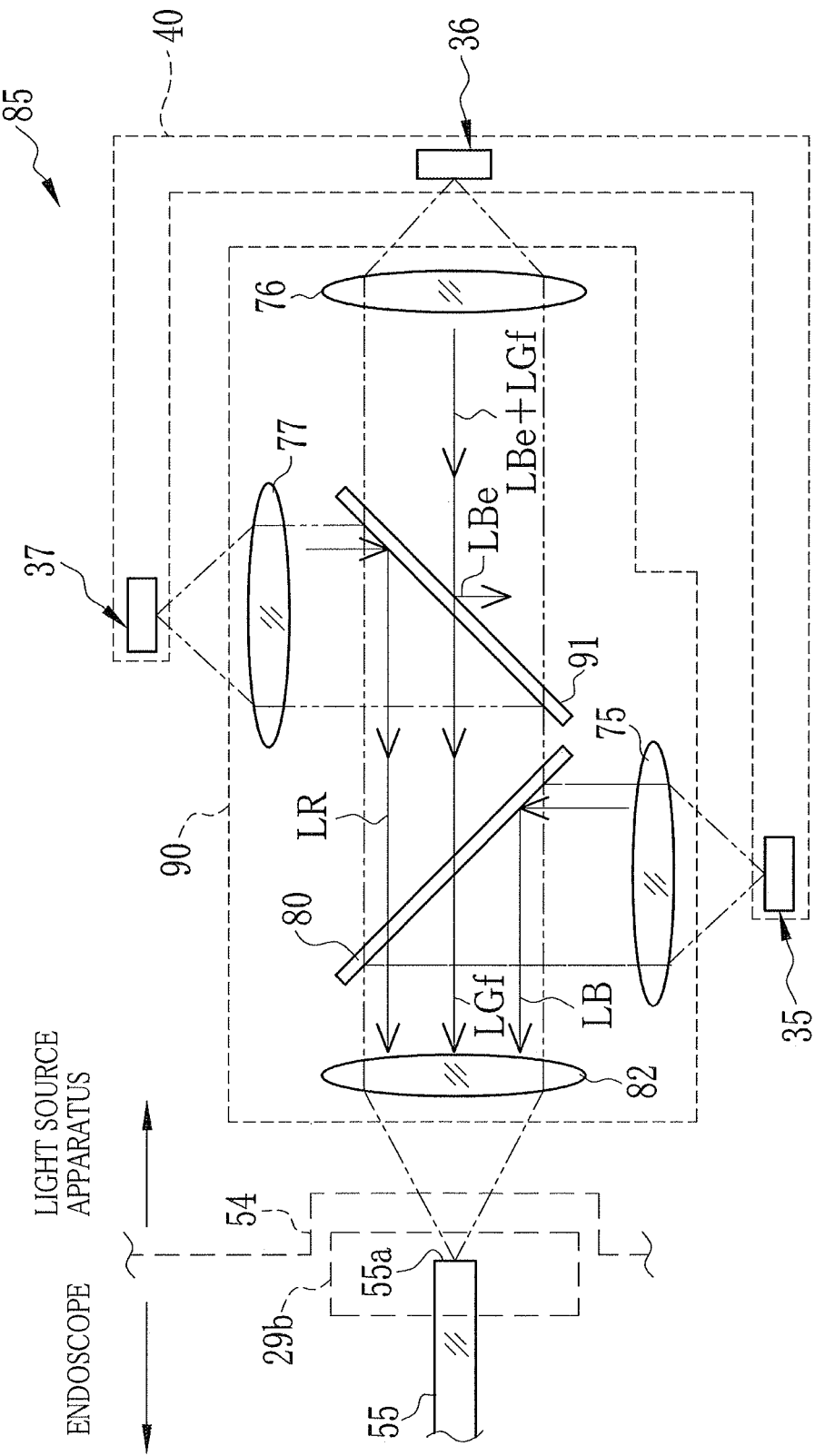
FIG. 21 is an explanatory view in a side elevation illustrating a second preferred embodiment in which a first dichroic mirror is disposed in a path coupler.

In FIG. 21, a path coupler 90 in a light source apparatus 85 includes a first dichroic mirror 91, which corresponds to the first dichroic mirror 79 of the first embodiment, and couples a light path of mixed light of the blue excitation light LBe and green fluorescence LGf from the green light source 36 with a light path of the red light LR from the red light source 37. A dichroic filter in the first dichroic mirror 91 operates also as an excitation light cut-off filter. In the path coupler 90, the path coupler 41 is repeated except for having the first dichroic mirror 91 instead of the first dichroic mirror 79.

Figure 22:
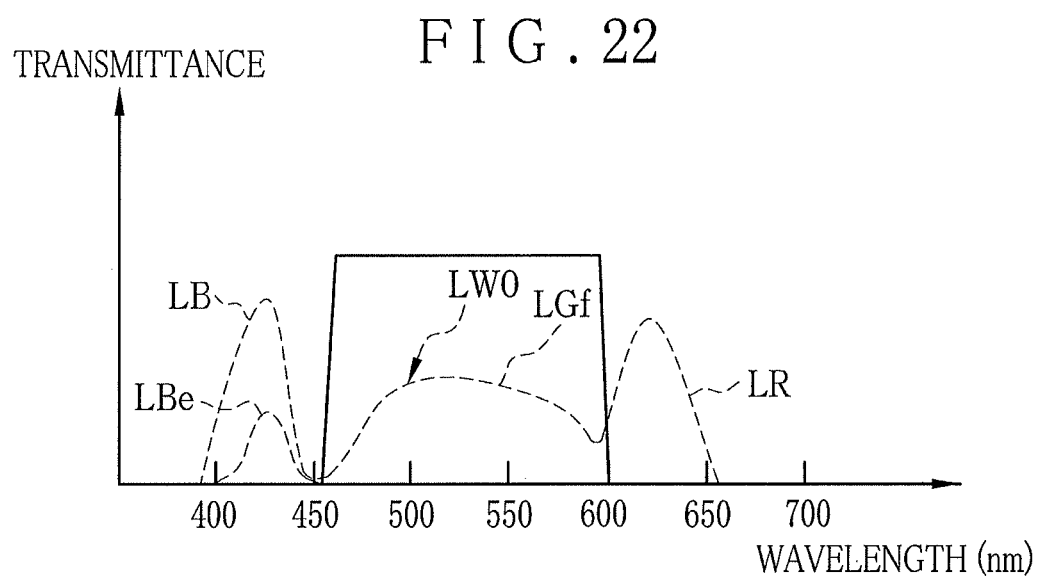
FIG. 22 is a graph illustrating a transmission characteristic of the dichroic filter in the first dichroic mirror.

As illustrated in FIG. 22, the dichroic filter of the first dichroic mirror 91 is caused to have a characteristic of reflecting light of a red wavelength range equal to or more than approximately 600 nm and light of a violet to blue wavelength range less than approximately 460 nm, and passing other light of a green wavelength range. In other words, the dichroic filter comes to have the band-pass characteristic of combining transmission characteristics of the first and second dichroic mirrors 79 and 80 in the first embodiment. However, there is a shortcoming of a high manufacturing cost of this band-pass characteristic in comparison with a short pass filter of transmitting light of only a short wavelength side or a long pass filter of transmitting light of only a long wavelength side. The structure of the first embodiment has an advantage in a lower cost, in that the dichroic filter in the second dichroic mirror 80 of a long pass characteristic has a function of the excitation light cut-off filter.

Third Preferred Embodiment

Figure 23:
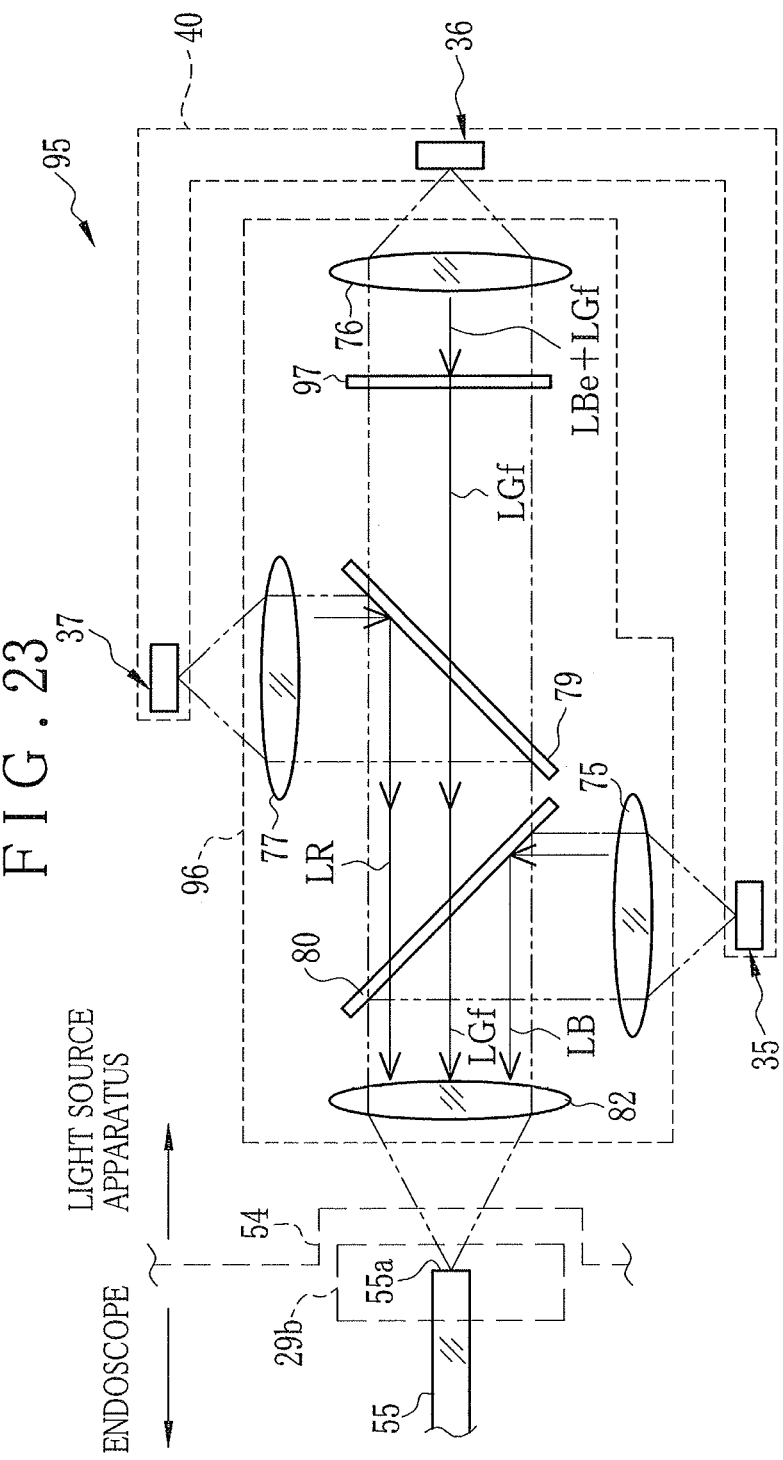
FIG. 23 is an explanatory view in a side elevation illustrating a third preferred embodiment with a wavelength cut-off filter.
Figure 24:
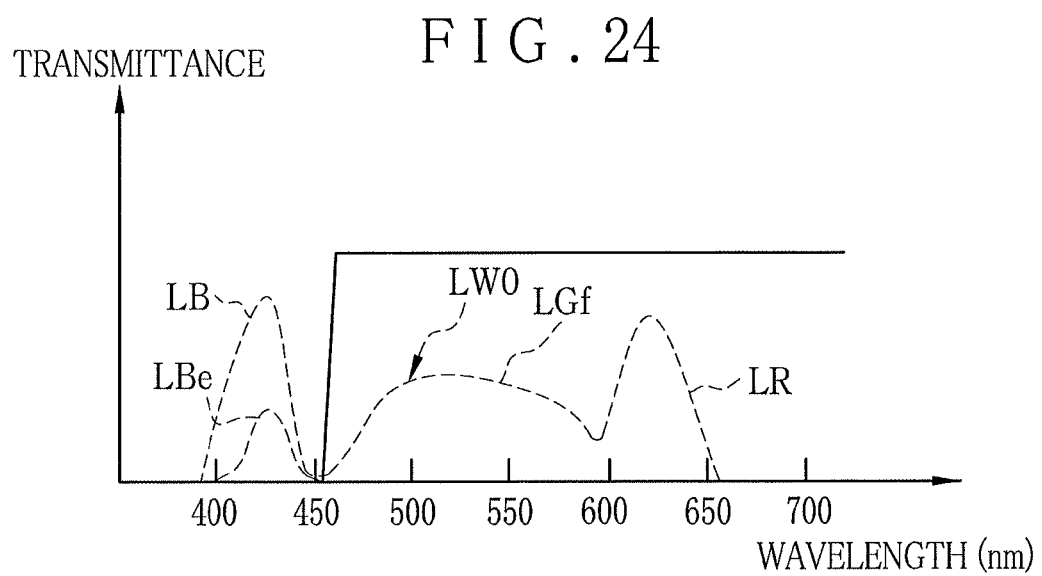
FIG. 24 is a graph illustrating a transmission characteristic of the wavelength cut-off filter.

In FIG. 23, another preferred light source apparatus 95 is illustrated. A path coupler 96 has a dichroic mirror and an excitation light cut-off filter separate from the dichroic mirror. A wavelength cut-off filter 97 or excitation light cut-off filter (or reduction filter) is disposed between the green light source 36 and the first dichroic mirror 79. In FIG. 24, the wavelength cut-off filter 97 reflects light of a violet to blue wavelength range less than approximately 460 nm, and passes light of a green to red wavelength range other than the same. Furthermore, the wavelength cut-off filter 97 may be disposed between the first and second dichroic mirrors 79 and 80. In conclusion, entry of the blue excitation light LBe to the entrance end 55a of the light guide device 55 should be prevented. An excitation light cut-off filter can be disposed between the blue excitation light source device 44 and the light guide device 55, and more precisely, a coupling position (intersection point) of coupling a light path of mixed light of the blue excitation light LBe and green fluorescence LGf from the green light source 36 and a light path of the blue light LB from the blue light source 35, or a position upstream from the coupling position in the light path.

Fourth Preferred Embodiment

In the first embodiment, the current values for the LEDs 43-45 are controlled. However, a light amount of a semiconductor light source relative to a current value of driving may be changed by influence of various factors, including heat generated by LEDs or phosphor or degradation with time. In the fourth embodiment, measurement sensors are used for measuring light amounts of the colors, to monitor a reach of the light amounts of the colors to a target value according to an output signal from the measurement sensors.

Figure 25:
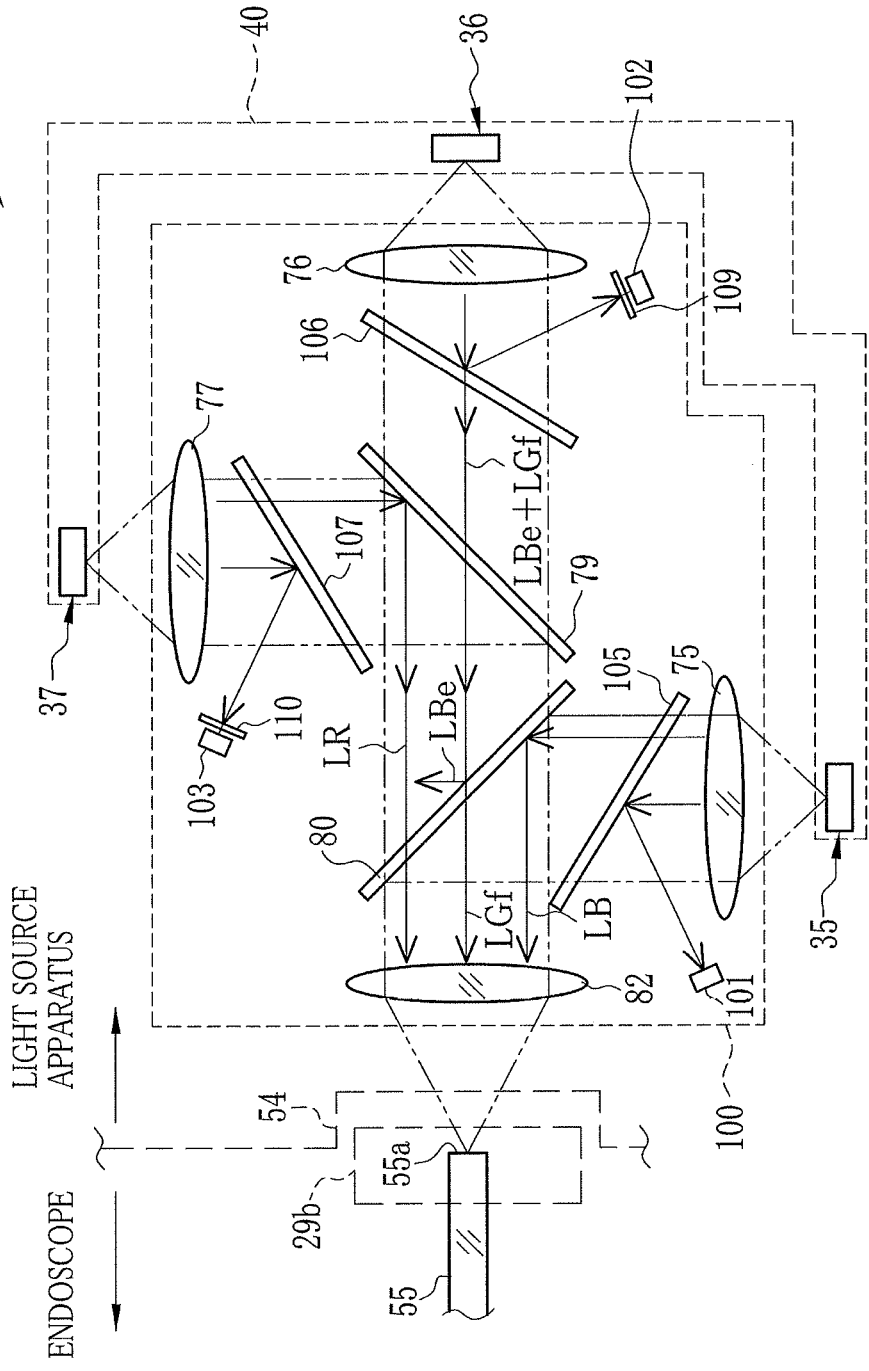
FIG. 25 is an explanatory view in a side elevation illustrating a fourth preferred embodiment with measurement sensors for light amounts.

In FIG. 25, a path coupler 100 in a light source apparatus 99 has the elements in the path coupler 41 of FIG. 18, and also includes a blue measurement sensor 101, a green measurement sensor 102 and a red measurement sensor 103 for light amounts, and glass plates 105, 106 and 107. The measurement sensors 101-103 measure the light amounts of the light of the colors from the B, G and R light sources 35-37. The glass plates 105-107 are disposed directly downstream of respectively the B, G and R light sources 35-37, and partially reflect light from the B, G and R light sources 35-37, to guide the light toward the measurement sensors 101-103.

The glass plates 105-107 are inclined with an angle of approximately 35 degrees with reference to the optical axes of the B, G and R light sources 35-37. The glass plates 105-107 pass light of the colors from the B, G and R light sources 35-37. There occurs Fresnel reflection upon incidence of the light on the glass plates 105-107. The glass plates 105-107 (optical path devices) guide partial light (as small as 4-8%) included in the light from the B, G and R light sources 35-37 toward the measurement sensors 101-103 by utilizing the Fresnel reflection. Also, it is possible to use other optical path devices such as optical fibers or the like, instead of the glass plates.

Figure 26:
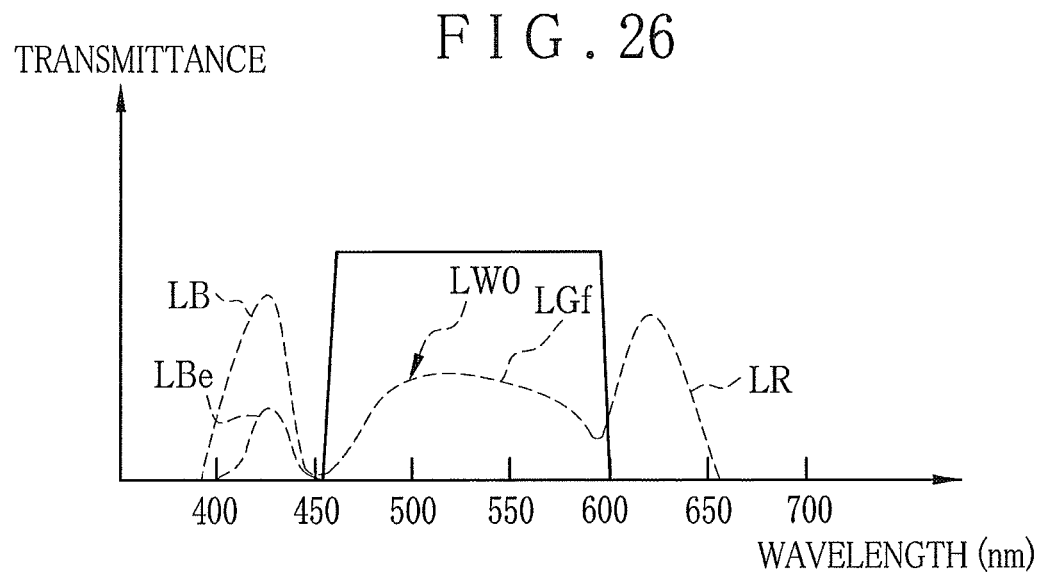
FIGS. 26 and 27 are graphs illustrating transmission characteristics of filters disposed upstream of the green and red measurement sensors.

A band pass filter 109 and a long pass filter 110 are disposed upstream of respectively the measurement sensors 102 and 103. The band pass filter 109 at the green measurement sensor 102 converts light into light of a limited wavelength range of the green fluorescence LGf constituting the illumination light LW0 and LW1 for final supply to the endoscope 11. In FIG. 26, the band pass filter 109 has a transmission characteristic of reflecting light of a red wavelength range equal to or more than approximately 600 nm and light of a violet to blue wavelength range less than approximately 460 nm, and passing light of a green wavelength range other than those wavelength ranges. In short, the band pass filter 109 has a band pass characteristic in combination of the transmission characteristics of the first and second dichroic mirrors 79 and 80 of the first embodiment, in a manner similar to the first dichroic mirror 91. The band pass filter 109 causes entry of the green fluorescence LGf to the green measurement sensor 102 after cutting off the blue excitation light LBe as a partial component of the illumination light LW0 and LW1. It is possible to measure the light amount of the green fluorescence LGf precisely.

Figure 27:
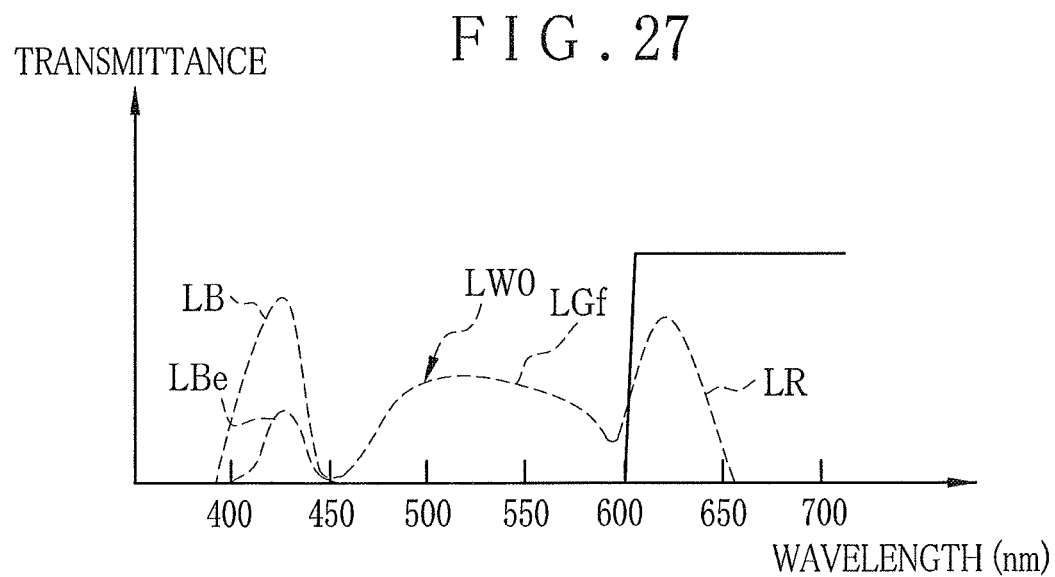

The long pass filter 110 at the red measurement sensor 103 converts light into light of a limited wavelength range of the red light LR constituting the light LW0 for final supply to the endoscope 11. In FIG. 27, the long pass filter 110 has a transmission characteristic of reflecting light of a green to blue wavelength range less than approximately 600 nm and passing light of a red wavelength range more than 600 nm. In short, the transmission characteristic of the long pass filter 110 is opposite to the transmission characteristic of the first dichroic mirror 79 of the first embodiment as illustrated in FIG. 19. In operation of the long pass filter 110, only the red light LR output as a part of the illumination light LW0 becomes incident upon the red measurement sensor 103. Thus, a light amount of the red light LR can be measured with precision.

Figure 28:
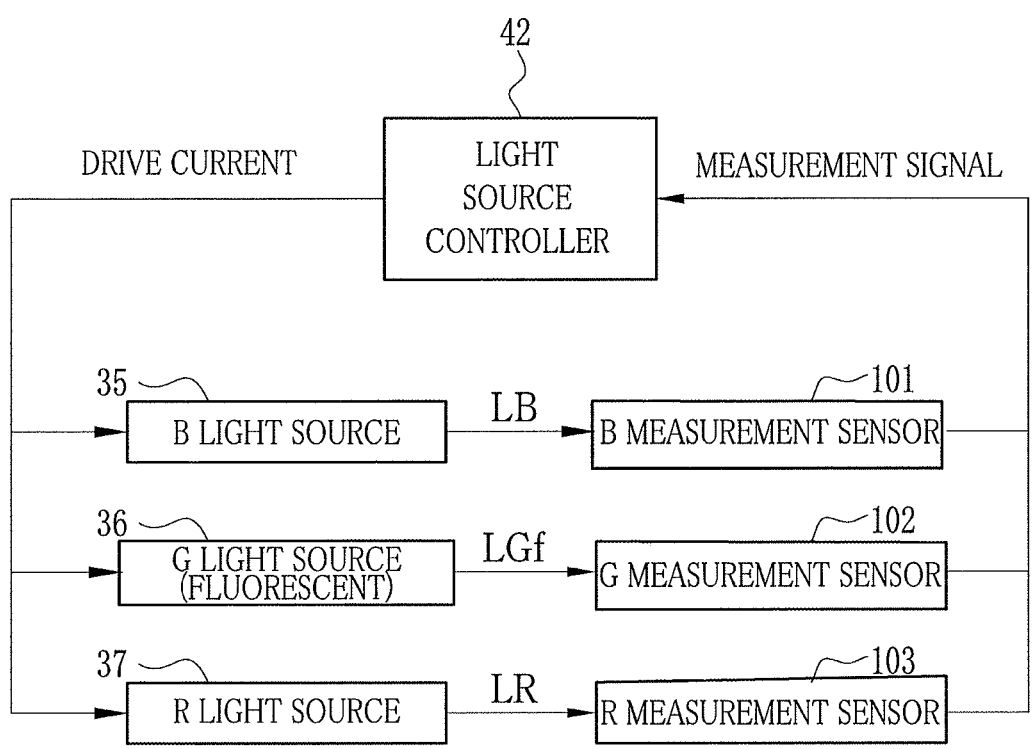
FIG. 28 is a block diagram schematically illustrating light amount control with the measurement sensors.

In FIG. 28, the measurement sensors 101-103 receive light of the colors guided by the glass plates 105-107 of the Fresnel reflection, and output measurement signals to the light source controller 42 according to light amounts of the colors. The light source controller 42 compares each of the measurement signals to a reference signal of a target light amount, and finely adjusts the current values of the drive currents for the B, G and R light sources 35-37 according to the exposure control to set the light amounts equal to the target light amount according to the comparison. This is effective in constantly controlling the light amounts by monitoring with the measurement sensors 101-103 and the fine adjustment of the current values. The light of a spectrum of the target can be obtained with high stability.

Figure 29:
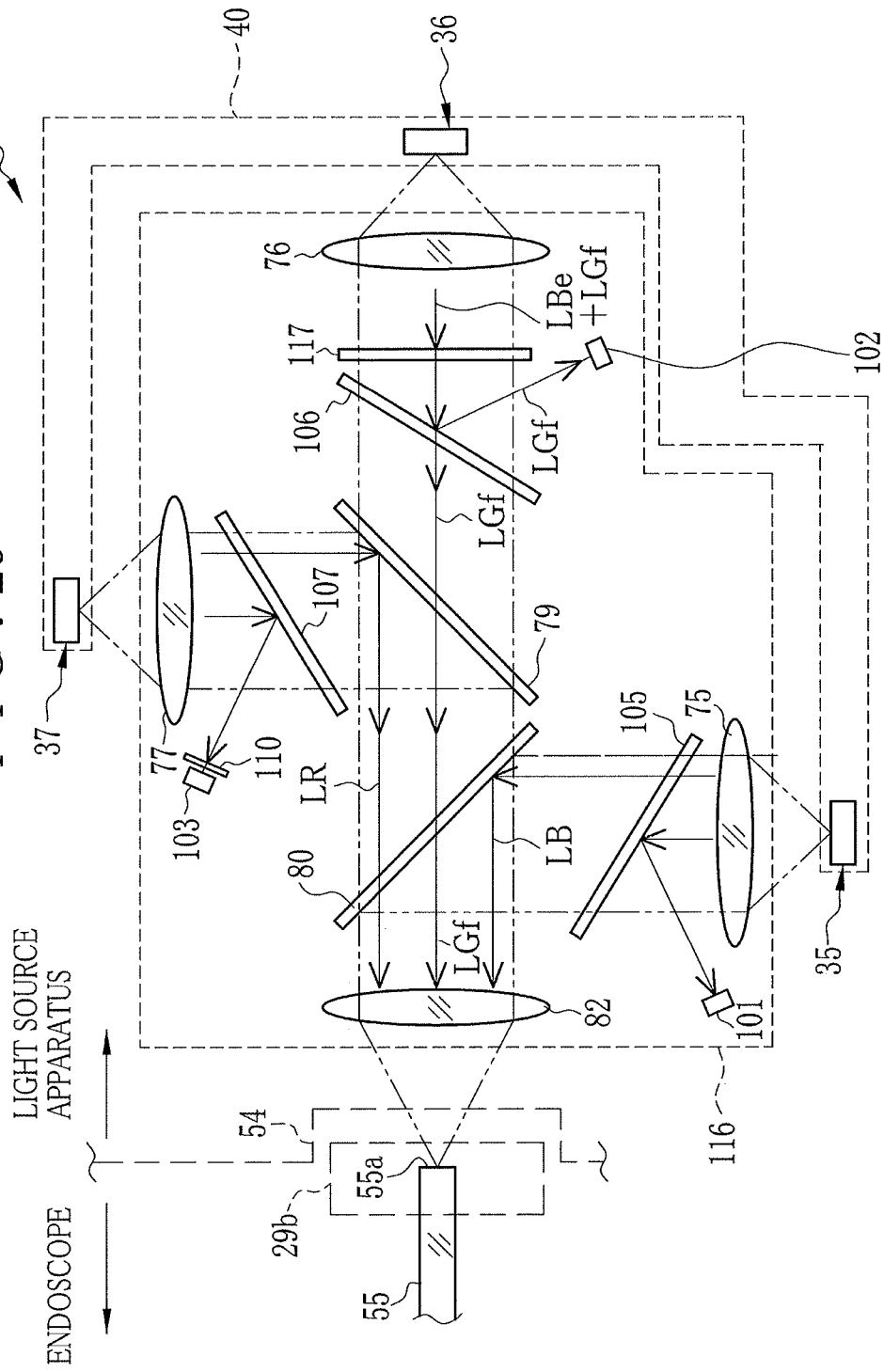
FIG. 29 is an explanatory view in a side elevation illustrating a path coupler having the measurement sensors.

In FIG. 29, another preferred light source apparatus 115 is illustrated. A path coupler 116 has a wavelength cut-off filter 117 or excitation light cut-off filter (or reduction filter) at a plate shape disposed between the green light source 36 and the first dichroic mirror 79 (the position of the wavelength cut-off filter 97 of the third embodiment in FIG. 23) with the same transmission characteristic as the band pass filter 109. Thus, it is unnecessary to use the band pass filter 109. However, there is a shortcoming in that a size of the wavelength cut-off filter 117 is larger than the band pass filter 109. The use of the band pass filter 109 is advantageous in view of reducing a cost and saving a space in comparison with the wavelength cut-off filter 117.

In the fourth embodiment, the measurement sensors are used for all of the semiconductor light sources. However, it is possible only to use the measurement sensor for the green light source 36, but not to use measurement sensors for the remaining semiconductor light sources, as a change in the light amount relative to the current value is remarkably large in the green light source 36.

In the fourth embodiment, the measurement sensors 101-103 measure light amounts downstream of the collimator lenses 75-77. However, the light amounts may be measured between the collimator lenses 75-77 and the B, G and R light sources 35-37 by use of the measurement sensors 101-103. Components of the light of the colors are diffused light, so that the measurement sensors 101-103 can directly measure the light amounts from the B, G and R light sources 35-37. Thus, it is unnecessary to dispose the glass plates 105-107 as an optical path device for guiding light.

Fifth Preferred Embodiment

The blue light source 35 in the above embodiments is a single device with its wavelength range and peak wavelength. Another preferred embodiment has a plurality of blue light sources of which the wavelength range and peak wavelength are different from one another. Those light sources are used in a distinct manner from one another by considering a state of surface blood vessels.

Figure 30:
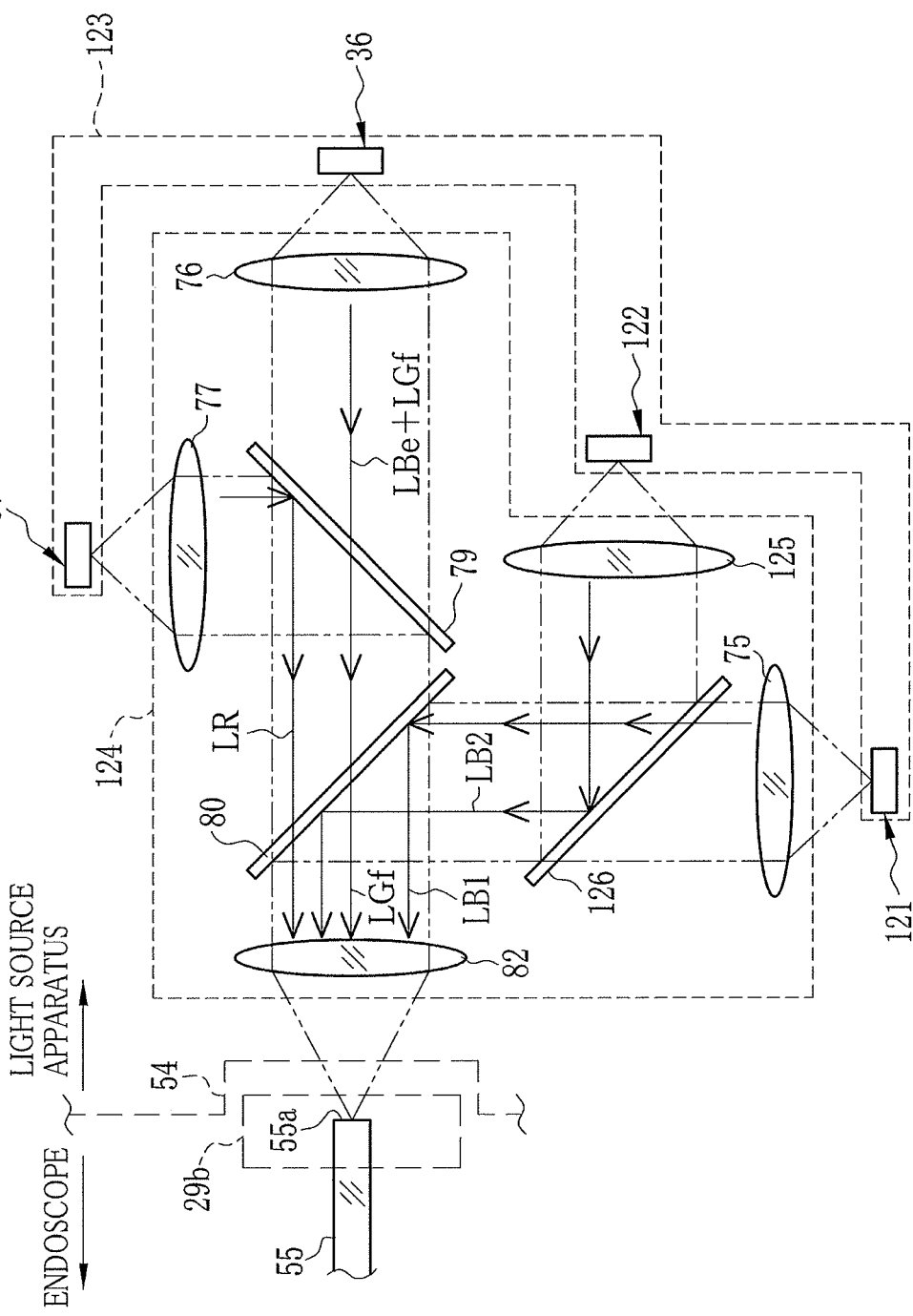
FIG. 30 is an explanatory view in a side elevation illustrating a fifth preferred embodiment having first and second blue semiconductor light sources.

In FIG. 30, a light source apparatus 120 includes a light source unit 123 and a path coupler 124. The light source apparatus 120 has the green and red light sources 36 and 37, and also a first blue light source 121 and a second blue light source 122 of a semiconductor. The path coupler 124 couples light paths from the blue and green light sources 35 and 36 and the blue light sources 121 and 122. The first blue light source 121 is present in place of the blue light source 35 of the above embodiments. For remaining parts, the first embodiment is repeated. Elements similar to those of the above embodiments are designated with identical reference numerals.

Figure 31:
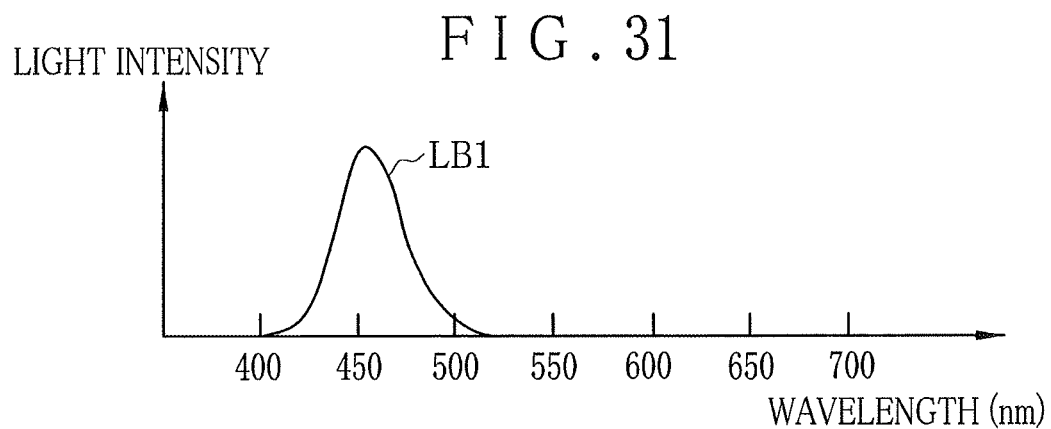
FIGS. 31 and 32 are graphs illustrating spectra of first and second blue light from the first and second blue light sources.
Figure 32:
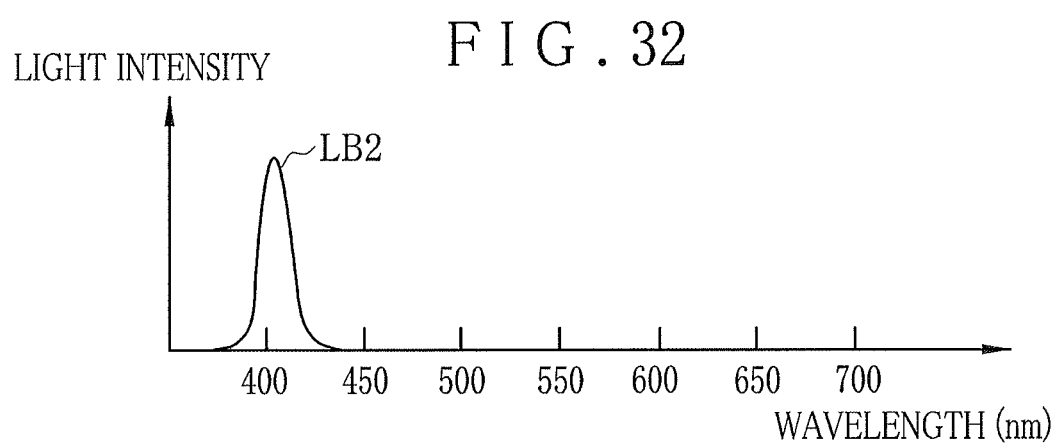

For the blue light sources 121 and 122, the form of the blue light source 35 in FIG. 4 is repeated. In FIG. 31, the first blue light source 121 emits first blue light LB1 having a component of 400-470 nm as a blue wavelength range, and a peak wavelength of 460 plus or minus 10 nm. In FIG. 32, the second blue light source 122 emits second blue light LB2 having a component of 395-415 nm as a violet to blue wavelength range, and a peak wavelength of 405 plus or minus 10 nm.

Figure 33:
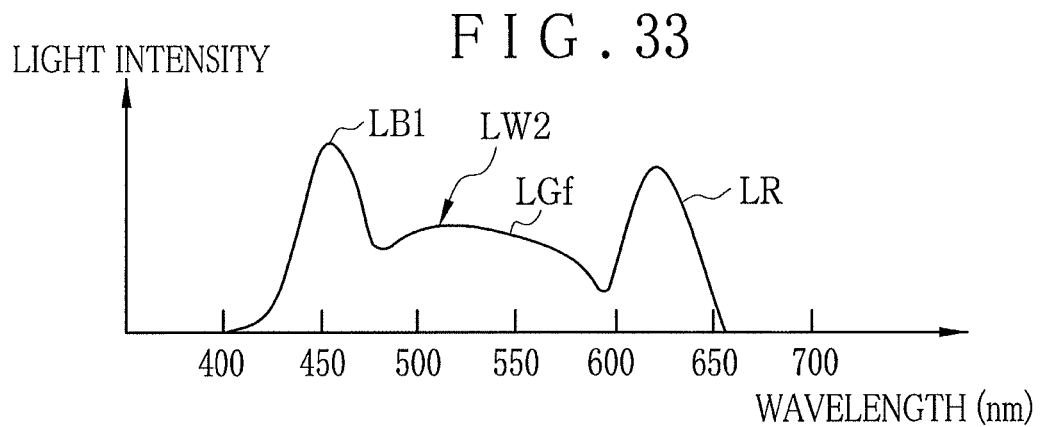
FIG. 33 is a graph illustrating a spectrum of white light.

The path coupler 124 includes the path coupler 41, a collimator lens 125 and a third dichroic mirror 126. The collimator lens 125 collimates the second blue light LB2 from the second blue light source 122. The collimator lens 125 couples light paths of the first blue light LB1 from the first blue light source 121 and the second blue light LB2 from the second blue light source 122. The path coupler 124 combines the light paths of the first and second blue light LB1 and LB2, green fluorescence LGf and red light LR to form one light path. In FIG. 33, a spectrum of the mixed light of the first blue light LB1, green fluorescence LGf and red light LR downstream of the path coupler 124 is illustrated. The mixed light is used as the illumination light LW2 in the embodiment for the normal imaging mode.

Figure 34:
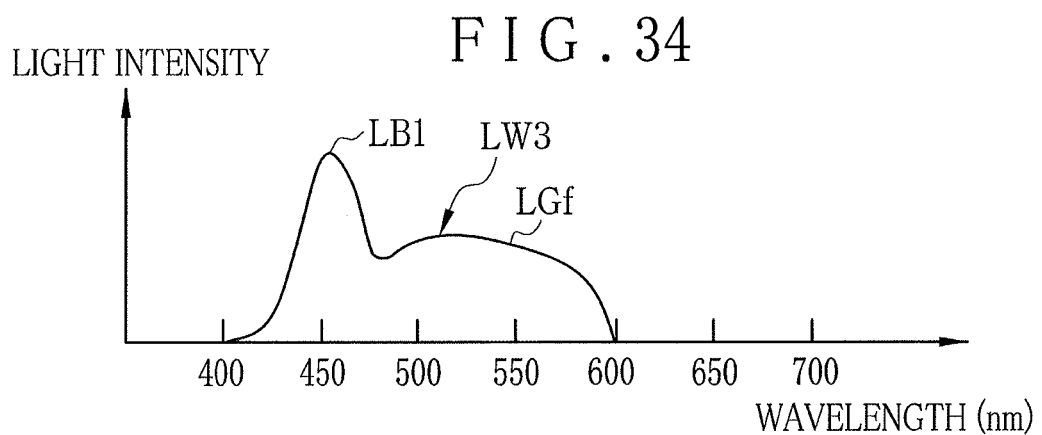
FIGS. 34 and 35 are graphs illustrating spectra of illumination light containing the first and second blue light and the green fluorescence.
Figure 35:
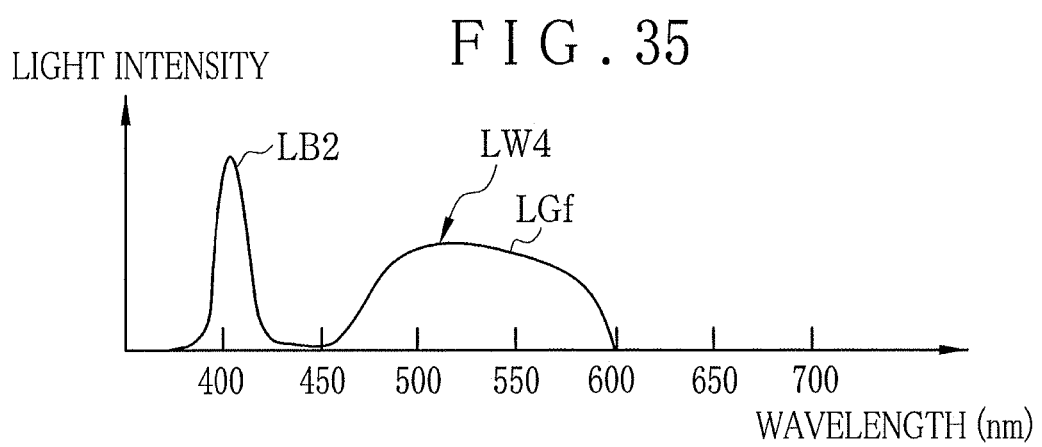

In FIG. 34, a spectrum of mixed light of the first blue light LB1 and green fluorescence LGf is illustrated. In FIG. 35, a spectrum of mixed light of the second blue light LB2 and green fluorescence LGf is illustrated. The illumination light LW3 and LW4 is utilized in the present embodiment for the vessel enhancement imaging mode by way of the mixed light in FIGS. 34 and 35.

The blue light sources 121 and 122 are so disposed that their light paths extend perpendicularly with one another. The third dichroic mirror 126 is positioned at a point of the intersection of those light paths. The third dichroic mirror 126 is oriented with an inclination of 45 degrees with reference to the blue light sources 121 and 122.

Figure 36:
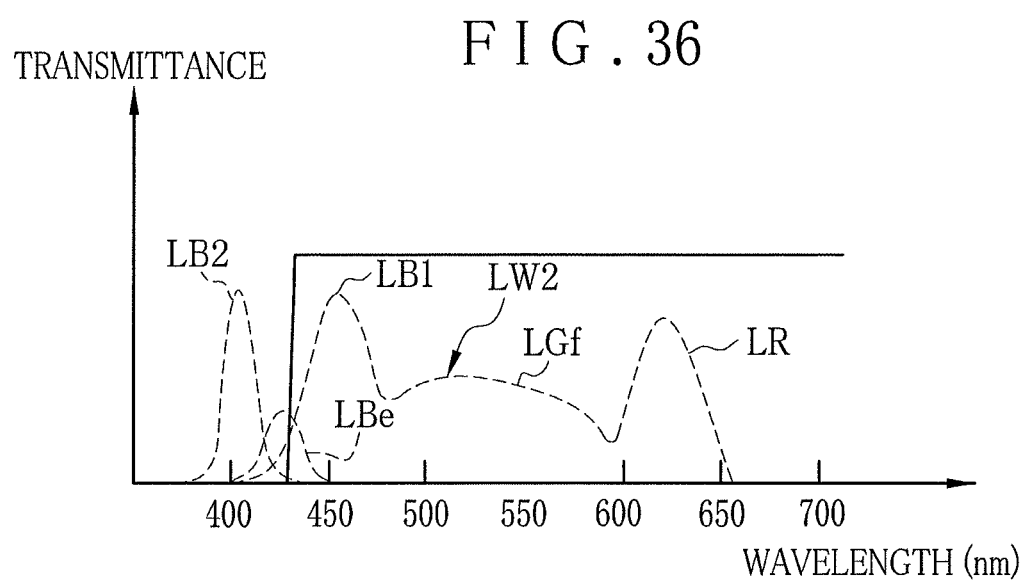
FIG. 36 is a graph illustrating a transmission characteristic of a dichroic filter in a third dichroic mirror.

In FIG. 36, the dichroic filter of the third dichroic mirror 126 has a transmission characteristic of reflecting light of a violet wavelength range less than approximately 430 nm and passing light of a blue, green and red wavelength range more than the same. The third dichroic mirror 126 passes the first blue light LB1 from the first blue light source 121 through the collimator lens 75, and reflects the second blue light LB2 from the second blue light source 122 through the collimator lens 125. Thus, light paths of the blue light LB1 and LB2 are coupled together. In FIG. 20, the second dichroic mirror 80 has a transmission characteristic of reflecting light of a blue wavelength range less than approximately 460 nm. Thus, the second blue light LB2 reflected by the third dichroic mirror 126 is reflected by the second dichroic mirror 80 and directed to the condenser lens 82. Consequently, all of the light paths of the blue light LB1 and LB2, green fluorescence LGf and red light LR are coupled together.

The absorption coefficient μa of hemoglobin in blood comes to the peak at approximately 405 nm, as has been described with FIG. 9. Light applied to an object of interest has a small depth of penetration according to smallness of the wavelength. See FIG. 10. The first blue light LB1 from the first blue light source 121 with the central wavelength of 460 plus or minus 10 nm has a relatively large depth of penetration with a relatively large wavelength, and is absorbed in mucosal blood vessels (medium deep) disposed at a lamina propria of the mucosa more than in surface blood vessels as a target of the above embodiment. Thus, the first blue light LB1 is used as special light for enhancement of the mucosal blood vessels. In contrast, the second blue light LB2 from the second blue light source 122 with the central wavelength of 405 plus or minus 10 nm has a relatively small depth of penetration with a relatively small wavelength, and is absorbed in subsurface blood vessels disposed at an epithelium (mucosa surface). Thus, the second blue light LB2 is used as special light for enhancement of the subsurface blood vessels. The blue light sources 121 and 122 are switched on and off selectively to use the blue light LB1 and LR2, so that a vessel enhancement image can be obtained with high contrast of the mucosal blood vessels or the subsurface blood vessels.

Figure 37:
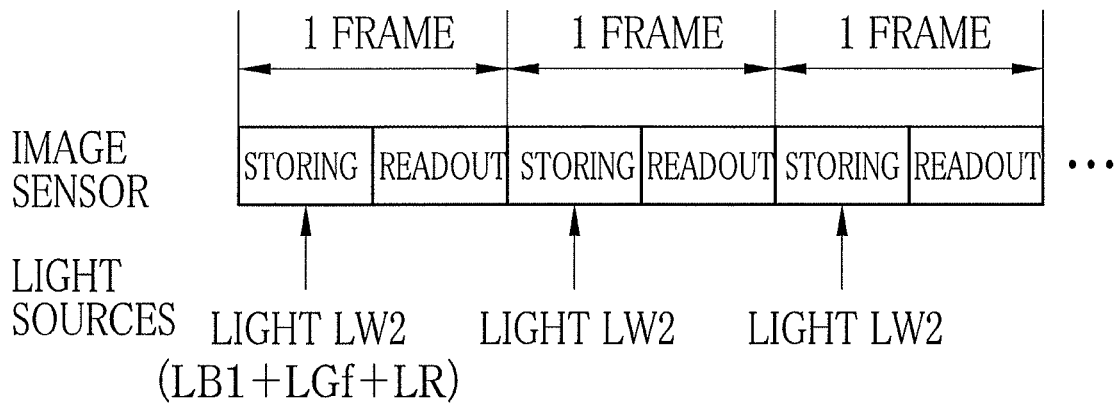
FIG. 37 is a timing chart illustrating lighting and imaging according to the normal imaging.
Figure 38:
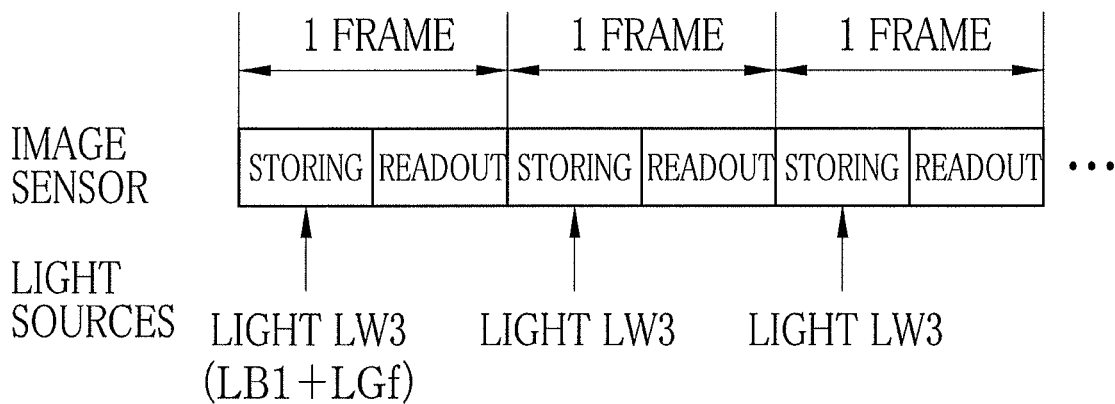
FIGS. 38 and 39 are timing charts illustrating lighting and imaging according to the vessel enhancement imaging of mucosal blood vessels and according to the vessel enhancement imaging of subsurface blood vessels.
Figure 39:
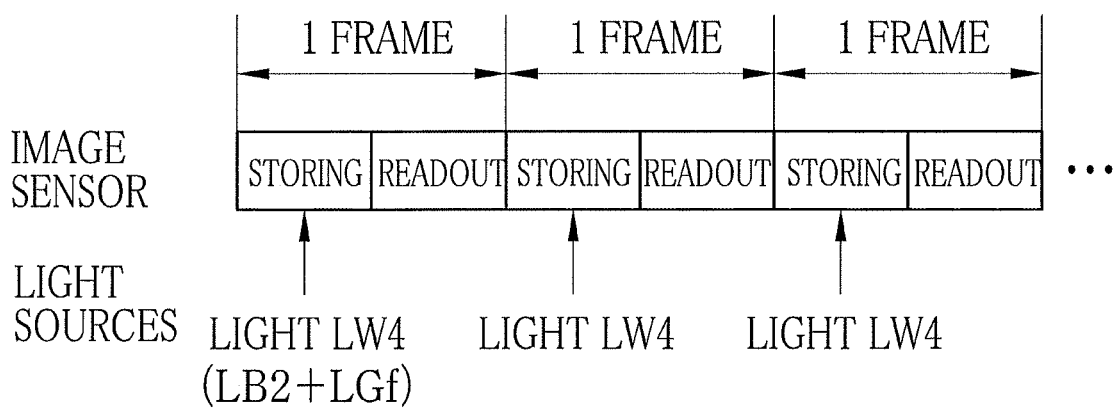

In FIG. 37, the green and red light sources 36 and 37 and the first blue light source 121 in the normal imaging mode are turned on according to a time point of the storing of the image sensor 56, to apply the illumination light LW2 (LB1+LGf+LR) to an object of interest, the illumination light LW2 being mixture of the first blue light LB1, green fluorescence LGf and red light LR. In FIG. 38, the green light source 36 and the first blue light source 121 in the vessel enhancement imaging of mucosal blood vessels (medium deep) are turned on according to a time point of the storing of the image sensor 56, to apply the illumination light LW3 (LB1+LGf) to an object of interest, the illumination light LW3 being mixture of the first blue light LB1 and green fluorescence LGf. In FIG. 39, the green light source 36 and the second blue light source 122 in the vessel enhancement imaging of subsurface blood vessels are turned on according to a time point of the storing of the image sensor 56, to apply the illumination light LW4 (LB2+LGf) to an object of interest, the illumination light LW4 being mixture of the second blue light LB2 and green fluorescence LGf.

Each component of the light LW2-LW4 is separated by the micro color filters in the image sensor 56. Reflected light corresponding to the blue light LB1 and LB2 is mainly received by the B pixels. Reflected light corresponding to the green fluorescence LGf is mainly received by the G pixels. Reflected light corresponding to the red light LR is mainly received by the R pixels. The image sensor 56 sequentially outputs the image signals B, G and R at the frame rate according to a time point of the readout.

The image signal B contains a component of reflected light corresponding to the first or second blue light LB1 or LB2, so that mucosal blood vessels (medium deep) or subsurface blood vessels can be expressed with high contrast. In a manner similar to surface blood vessels, vessel density between the mucosal blood vessels or subsurface blood vessels is likely to be higher in a lesion of a cancer or the like than that in normal body tissue. Thus, the feature of the light source apparatus 120 in the embodiment is effective in clearly expressing the mucosal blood vessels or subsurface blood vessels with a specifically patterned form in the mucosal blood vessels or subsurface blood vessels.

In the above embodiments, the peak wavelengths of blue light are 430, 405 and 460 nm. However, a peak wavelength of blue light from a blue light source can be 415 nm.

Especially, the wavelengths 405, 415 and 430 nm are characterized in that the absorption coefficient μa of hemoglobin in blood is high in the absorption spectrum of the hemoglobin in blood in FIG. 9. Therefore, a vessel enhancement image can be obtained with enhanced contrast between blood vessels and other tissue. Should a balance of the spectrum of light for the vessel enhancement imaging be lost in use of the blue excitation light LBe from the green light source 36, serious influence occurs to the imaging due to changes in color balance of the vessel enhancement image.

It follows that cutting off the blue excitation light LBe from the green light source 36 with the excitation light cut-off filter (wavelength cut-off filter component) is effective typically in case a peak wavelength of blue light from a blue light source is one of 405, 415 and 430 nm.

Figure 40:
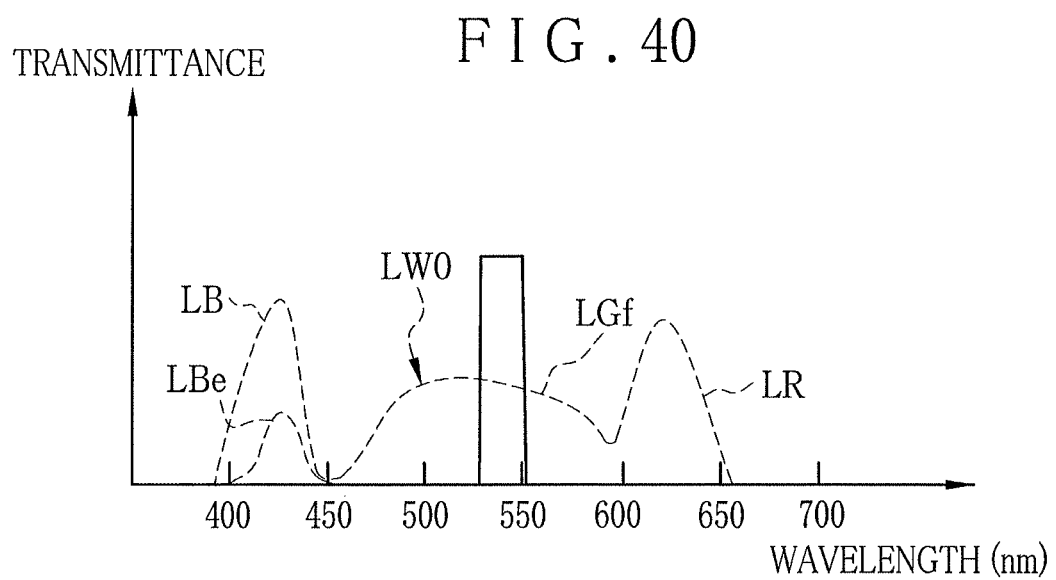
FIG. 40 is a graph illustrating a transmission characteristic of a wavelength cut-off filter.

In FIG. 40, a transmission characteristic of another example is illustrated. The wavelength cut-off filter 97 of the third embodiment or the wavelength cut-off filter 117 of the fourth embodiment can have the transmission characteristic as depicted. This is a narrow band filter of green with a band pass characteristic of reflecting light of a green and red wavelength range equal to or more than approximately 550 nm and light of a green and blue wavelength range less than approximately 530 nm, and passing other light of a green wavelength range. The excitation light cut-off filter of this transmission characteristic can cut off the blue excitation light LBe and obtain light of a wavelength range of 530-550 nm included in the green fluorescence LGf, so that contrast of subsurface or deep blood vessels in the display image can be enhanced.

To this end, a filter moving mechanism is disposed for moving the excitation light cut-off filter between an active position in a light path of the green light source 36 and an inactive position set out of the light path of the green light source 36. In the normal imaging mode, the excitation light cut-off filter is shifted to the inactive position. In the vessel enhancement imaging mode, the excitation light cut-off filter is shifted to the active position.

The mounting method of the LEDs in the invention is not limited to the first embodiment. For example, a micro lens can be disposed on an exit surface of the resin encapsulant 35c or the green emitting phosphor 47 in FIGS. 4 and 5 for adjusting an angle of divergence. Also, a housing of a bullet shape including a micro lens can be used for containing an LED in place of the surface mounting type. In the above embodiments, the green emitting phosphor 47 and the blue excitation light source device 44 are both mounted on the semiconductor substrate 36a by way of the green light source 36. However, the green emitting phosphor 47 can be separate from the semiconductor substrate 36a. To this end, guiding optics such as a lens or fiber optics can be added between the blue excitation light source device 44 and the green emitting phosphor 47, to guide excitation light from the blue excitation light source device 44 to the green emitting phosphor 47.

Sixth Preferred Embodiment

In FIG. 41, another preferred light source apparatus includes a blue excitation light source device or light source LD 131 (light source laser diode), in place of the LED. A fluorescent type of green light source 130 of a semiconductor includes the light source LD 131 and green emitting phosphor 132 disposed downstream of the light source LD 131. The green light source 130 is used in place of the green light source 36 of the above embodiments.

For this purpose, a transparent rotatable disk 133 is prepared. A coating is applied to a surface of the rotatable disk 133 to form the green emitting phosphor 132. A rotating mechanism 134 with a motor and the like rotates the rotatable disk 133. Blue excitation light from the light source LD 131 is applied to a point that is disposed eccentrically on the rotatable disk 133. Rotation of the rotatable disk 133 can prevent the excitation light from concentrating at one point on the green emitting phosphor 132. Should excitation light concentrate at one point on the green emitting phosphor 132, the point of the green emitting phosphor 132 will be overheated to quicken degradation of the green emitting phosphor 132. However, the feature of the embodiment can prevent such a difficulty. Note that a condenser lens 135 condenses the blue excitation light from the light source LD 131 on the rotatable disk 133.

Also, an excitation light cut-off filter (wavelength cut-off filter component) may be formed on an exit surface of the rotatable disk 133. It is possible to use an organic electro luminescence device (EL device) and the like may be used instead of the LEDs and LDs. Furthermore, the blue and red light sources 35 and 37 and the like other than the light source of a type with green emitting phosphor can be constituted by an LD, organic EL device and the like.

The excitation light cut-off filter for cutting all of the excitation light is used in the above embodiments. However, the invention is not limited to those embodiments. An excitation light cut-off filter (wavelength cut-off filter component) according to the invention can be an element with a transmission characteristic for reducing a light amount of the excitation light, for example, reducing the light amount by 50%. However, it is desirable for an excitation light cut-off filter to cut off 100% of the excitation light because of high effect.

The path coupler of the invention is not limited to the above embodiments. It is possible to use a dichroic prism including a prism and a dichroic filter formed thereon in place of the dichroic mirror. For the purpose of coupling the light paths, it is possible to use a light guide device of a branch form having plural entrance ends for light sources and one exit end directed to the entrance end of the light guide device of the endoscope, in place of the optics having the dichroic filter. The light guide device of the branch form is a fiber bundle of plural optical fibers. Proximal ends of the optical fibers are grouped at a predetermined number of fibers to form the plural entrance ends. Light sources of a semiconductor are disposed upstream of respectively the entrance ends. An excitation light cut-off filter is disposed between the fluorescent type of green light source and one of the entrance ends.

In the above embodiments, the image sensor is the color image sensor. However, an image sensor in an endoscope system of the invention may be a monochromatic image sensor. In the above embodiment, the lighting control is the simultaneous lighting (with normal white light), with which the color image sensor acquires image signals of B, G and R simultaneously. However, a lighting control in a light source apparatus can be field sequential lighting, in which blue, green and red light components are applied to an object of interest one after another, for a monochromatic image sensor to acquire image signals of B, G and R sequentially.

In FIG. 42, the field sequential lighting is illustrated. In the vessel enhancement imaging mode, the blue and green light sources 35 and 36 are turned on and off alternately according to time points of the storing of the image sensor. The blue light LB and the green fluorescence LGf are applied to an object of interest alternately. The image processor produces a vessel enhancement image of one frame according to image signals of two consecutive frames.

Furthermore, the lighting control in the endoscope system can be changeable between simultaneous lighting and field sequential lighting. In FIG. 15, the simultaneous lighting is set for emitting the mixed illumination light LW1 of the blue light LB and the green fluorescence LGf. In FIG. 42, the field sequential lighting is set for sequentially emitting the blue light LB and the green fluorescence LGf. It is possible to utilize advantages of both the simultaneous lighting and the field sequential lighting.

Furthermore, the features of the various embodiments can be combined with one another according to the present invention.

Furthermore, a light source apparatus with the feature of the invention can be a light source apparatus including a violet semiconductor light source (violet LED). In the above embodiments, the wavelength range of the blue light LB from the blue LED 43 overlaps on that of the blue excitation light LBe from the blue excitation light source device 44. Similarly, a wavelength range of violet light from the violet semiconductor light source is likely to overlap partially on that of the blue excitation light LBe from the blue excitation light source device 44. However, the feature of the invention is effective in preventing influence of the blue excitation light LBe to a light amount of the violet light.

In the above embodiments, the light source apparatus 13 is separate from the processing apparatus 12. However, a composite apparatus including components of the processing apparatus 12 and the light source apparatus 13 may be used in the invention. Furthermore, an endoscope and light source apparatus of the invention can be used with a fiber scope for guiding reflected light from an object of interest by use of an image guide, an ultrasonic endoscope including an image sensor and an ultrasonic transducer incorporated in the tip device.

According one embodiment mode of the invention, furthermore, a red semiconductor light source emits red light of a red wavelength range.

According another embodiment mode of the invention, the blue semiconductor light source emits the blue light with a peak wavelength of at least one of 405, 415, 430 and 460 nm.

According still another embodiment mode of the invention, the blue excitation light source device is a light emitting diode.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A light source apparatus for supplying a light guide device of an endoscope with light, comprising:

a first blue semiconductor light source for emitting first blue light;

a second blue semiconductor light source for emitting second blue light having a shorter wavelength than said first blue light;

a fluorescent type of a green semiconductor light source, having a blue excitation light source device and green emitting phosphor, said blue excitation light source device emitting blue excitation light having a peak wavelength between a peak wavelength of said first blue light and a peak wavelength of said second blue light, said green emitting phosphor being excited by said blue excitation light for emitting green fluorescence of a green wavelength range;

a red semiconductor light source for emitting red light of a red wavelength range;

a first dichroic filter having a short pass or long pass characteristic, which outputs said blue excitation light and said green fluorescence from said green semiconductor light source and said red light from said red semiconductor light source in a same direction;

a third dichroic filter having a short pass or long pass characteristic, which outputs said first blue light from said first blue semiconductor light source and said second blue light from said second blue semiconductor light source in a same direction; and a second dichroic filter having a short pass or long pass characteristic, which outputs said green fluorescence and said red light from said first dichroic filter and said first blue light and said second blue light from said third dichroic filter toward said light guide device, and outputs said blue excitation light from said first dichroic filter in a direction away from said light guide device.

2. A light source apparatus as defined in claim 1, further comprising a driver for simultaneously driving said first blue semiconductor light source and said green semiconductor light source to output mixed light of said first blue light and said green fluorescence, or simultaneously driving said second blue semiconductor light source and said green semiconductor light source to output mixed light of said second blue light and said green fluorescence, for vessel enhancement imaging.

3. A light source apparatus as defined in claim 1, further comprising a driver for alternately driving said first blue semiconductor light source and said green semiconductor light source sequentially to output said first blue light and said green fluorescence, or alternately driving said second blue semiconductor light source and said green semiconductor light source sequentially to output said second blue light and said green fluorescence, for vessel enhancement imaging.

4. A light source apparatus as defined in claim 1, further comprising a driver, connected to said first and/or second blue semiconductor light source and said green semiconductor light source, and changeable between simultaneous lighting and field sequential lighting;

wherein in said simultaneous lighting, said driver simultaneously drives said first blue semiconductor light source and said green semiconductor light source to output mixed light of said first blue light and said green fluorescence, or simultaneously drives said second blue semiconductor light source and said green semiconductor light source to output mixed light of said second blue light and said green fluorescence, for vessel enhancement imaging;

in said field sequential lighting, said driver alternately drives said first blue semiconductor light source and said green semiconductor light source sequentially to output said first blue light and said green fluorescence, or alternately drives said second blue semiconductor light source and said green semiconductor light source sequentially to output said second blue light and said green fluorescence, for vessel enhancement imaging.

5. A light source apparatus as defined in claim 1, wherein said first blue semiconductor light source emits said first blue light with a peak wavelength of 430 nm or 460 nm, and said second blue semiconductor light source emits said second blue light with a peak wavelength of 405 nm.

6. A light source apparatus as defined in claim 1, further comprising:

a measurement sensor for measuring a light amount of said first or second blue light or said green fluorescence emitted by at least one of said first and second blue semiconductor light sources and green semiconductor light source;

an optical path device for guiding part of said first or second blue light or said green fluorescence to said measurement sensor;

a light source controller for controlling power supplied to said first or second blue or green semiconductor light source according to a measurement result of said measurement sensor.

7. A light source apparatus as defined in claim 6, wherein said measurement sensor and said optical path device are associated with said green semiconductor light source, and said light source controller adjusts said power supplied to said blue excitation light source device according to said measurement result.

8. A light source apparatus as defined in claim 7, further comprising a band pass filter, disposed upstream of said measurement sensor, for cutting off light with a wavelength different from said green wavelength range of said green fluorescence, from light emitted by said green semiconductor light source and reflected by said optical path device.

9. A light source apparatus as defined in claim 7, further comprising a wavelength cut-off filter of a plate shape disposed between said green semiconductor light source and said optical path device, for cutting off said blue excitation light.

10. A light source apparatus as defined in claim 6, wherein said optical path device includes a transparent glass plate, disposed downstream of said first or second blue semiconductor light source or green semiconductor light source, for reflecting said part of said first or second blue light or said green fluorescence by Fresnel reflection, to guide said part to said sensor.

11. A light source apparatus as defined in claim 1, further comprising a rotatable disk having said green emitting phosphor formed on a surface thereof;

wherein said blue excitation light source device emits said blue excitation light toward said rotatable disk being rotated at an eccentric point thereof.

12. A light source apparatus as defined in claim 1, wherein said blue excitation light source device is a light emitting diode.

13. An endoscope system including an endoscope having a light guide device for guiding light, and a light source apparatus for supplying said light guide device with said light, said endoscope system comprising:

said light source apparatus including:

a first blue semiconductor light source for emitting first blue light;

a second blue semiconductor light source for emitting second blue light having a shorter wavelength than said first blue light;

a fluorescent type of a green semiconductor light source, having a blue excitation light source device and green emitting phosphor, said blue excitation light source device emitting blue excitation light having a peak wavelength between a peak wavelength of said first blue light and a peak wavelength of said second blue light, said green emitting phosphor being excited by said blue excitation light for emitting green fluorescence of a green wavelength range;

a red semiconductor light source for emitting red light of a red wavelength range;

a first dichroic filter having a short pass or long pass characteristic, which outputs said blue excitation light and said green fluorescence from said green semiconductor light source and said red light from said red semiconductor light source in a same direction;

a third dichroic filter having a short pass or long pass characteristic, which outputs said first blue light from said first blue semiconductor light source and said second blue light from said second blue semiconductor light source in a same direction; and a second dichroic filter having a short pass or long pass characteristic, which outputs said green fluorescence and said red light from said first dichroic filter and said first blue light and said second blue light from said third dichroic filter toward said light guide device, and outputs said blue excitation light from said first dichroic filter in a direction away from said light guide device.

14. A light source apparatus as defined in claim 1, wherein said first dichroic filter has a short pass characteristic to pass said blue excitation light and said green fluorescence from said green semiconductor light source and reflect said red light from said red semiconductor light source, or a long pass characteristic to reflect said blue excitation light and said green fluorescence from said green semiconductor light source and pass said red light from said red semiconductor light source.

15. A light source apparatus as defined in claim 1, wherein said second dichroic filter has a long pass characteristic to pass said green fluorescence and said red light from said first dichroic filter and reflect said blue excitation light from said first dichroic filter and said first blue light and said second blue light from said third dichroic filter, or a short pass characteristic to reflect said green fluorescence and said red light from said first dichroic filter and pass said blue excitation light from said first dichroic filter and said first blue light and said second blue light from said third dichroic filter.

16. A light source apparatus as defined in claim 1, wherein said third dichroic filter has a long pass characteristic to pass said first blue light from said first blue semiconductor light source and reflect said second blue light from said second blue semiconductor light source, or a short pass characteristic to reflect said first blue light from said first blue semiconductor light source and pass said second blue light from said second blue semiconductor light source.

17. A light source apparatus as defined in claim 1, further comprising a light source controller for discretely changing a current value of driving said each semiconductor light source to increase or decrease a light amount of said each color light.

18. A light source apparatus as defined in claim 17, further comprising measurement sensors for measuring each light amount of said each color light, wherein said light source controller adjusts each current value of driving said each semiconductor light source according to a measurement result of said each measurement sensor.

* * * * *